United States Patent [19]

Mische et al.

[11] Patent Number: 5,792,157

[45] Date of Patent: *Aug. 11, 1998

[54] EXPANDABLE INTRAVASCULAR OCCLUSION MATERIAL REMOVAL DEVICES AND METHODS OF USE

[75] Inventors: Hans A. Mische; Thomas V. Ressemann, both of St. Cloud; Scott A. Hoium, Coon Rapids, all of Minn.

[73] Assignee: SciMed Life Systems, Inc., Maple Grove, Minn.

[*] Notice: The term of this patent shall not extend beyond the expiration date of Pat. No. 5,490,859.

[21] Appl. No.: 723,552

[22] Filed: Sep. 30, 1996

Related U.S. Application Data

[63] Continuation-in-part of Ser. No. 621,350, Mar. 25, 1996, which is a continuation-in-part of Ser. No. 206,053, Mar. 3, 1994, Pat. No. 5,501,694, which is a continuation-in-part of Ser. No. 261,813, Jun. 17, 1994, Pat. No. 5,540,707, which is a continuation-in-part of Ser. No. 55,995, Apr. 29, 1993, Pat. No. 5,490,859, which is a continuation-in-part of Ser. No. 976,199, Nov. 13, 1992, abandoned.

[51] Int. Cl.⁶ .................................................. A61B 17/22
[52] U.S. Cl. ........................... 606/159; 606/170; 606/180
[58] Field of Search ............................. 606/1, 159, 170, 606/171, 180, 191.2; 604/22, 104, 105

[56] References Cited

U.S. PATENT DOCUMENTS

| | | |
|---|---|---|
| 1,112,982 | 10/1914 | Conine . |
| 1,612,697 | 12/1926 | Cecil . |

(List continued on next page.)

FOREIGN PATENT DOCUMENTS

| | | |
|---|---|---|
| 0 117 519 1 | 2/1984 | European Pat. Off. . |
| 0 254 414 A1 | 6/1987 | European Pat. Off. . |

(List continued on next page.)

OTHER PUBLICATIONS

Technical Bulletin P.B.S. vs. Electroplating Abrasive Technology, Inc. from Manufacturers of Diamond and CBN Products for Industry.

(List continued on next page.)

*Primary Examiner*—William Lewis
*Attorney, Agent, or Firm*—Nawrocki, Rooney & Sivertson

[57] ABSTRACT

A novel intravascular occlusion material removal device for removing vascular occlusion material in a vascular lumen comprises a prime mover and an expandable material removal element insertable intravascularly into the vascular lumen. A hollow drive shaft operatively connects the prime mover to the expandable material removal element for rotating the expandable material removal element intravascularly. A guidewire is insertable through the distal end of the expandable material removal element and the hollow drive shaft, and is shiftable within the drive shaft and the expandable material removal element. The expandable material removal element is expandable responsive to shifting of the guidewire. A material removal element movement control mechanism is operatively connected to the guidewire for positively incrementally shifting the guidewire, and a guidewire lock mechanism is operatively connected between the guidewire and the material removal element movement control mechanism for fixing the guidewire with respect to the material removal element movement control mechanism. A number of novel methods for removing vascular occlusion material are also provided. One such method comprises the steps of: providing a vascular occlusion material removal device having an expandable occlusion material removal element, the material removal element comprising a braid having a hollow interior; providing a guidewire; intravascularly navigating the guidewire to the occlusion material; inserting the guidewire into the hollow interior; intravascularly navigating the braid to the occlusion material over the guidewire; shifting the guidewire with respect to the braid to expand the braid; expanding the braid such that the braid bites into occlusion material thereby allowing occlusion material to pass into the hollow interior; and shifting the guidewire with respect to the braid to contract the braid and to capture occlusion material within the hollow interior. The expanded braid can also be rotated intravascularly to remove occlusion material.

25 Claims, 6 Drawing Sheets

U.S. PATENT DOCUMENTS

| | | |
|---|---|---|
| 2,498,692 | 2/1950 | Mains . |
| 2,621,651 | 12/1952 | Wallace . |
| 2,816,552 | 12/1957 | Hoffman . |
| 3,352,303 | 11/1967 | Delaney . |
| 3,416,531 | 12/1968 | Edwards . |
| 3,433,226 | 3/1969 | Boyd . |
| 3,485,234 | 12/1969 | Stevens . |
| 3,568,659 | 3/1971 | Karnegis . |
| 3,605,725 | 9/1971 | Bentov . |
| 3,623,483 | 11/1971 | Dyer, Jr. . |
| 3,692,029 | 9/1972 | Adair . |
| 3,773,034 | 11/1973 | Burns et al. . |
| 3,788,318 | 1/1974 | Kim et al. . |
| 3,789,852 | 2/1974 | Kim et al. . |
| 3,868,956 | 3/1975 | Alfidi et al. . |
| 3,894,673 | 7/1975 | Lowder et al. . |
| 3,923,065 | 12/1975 | Nozick et al. . |
| 3,965,909 | 6/1976 | Waddell et al. . |
| 3,968,800 | 7/1976 | Vilasi . |
| 3,996,938 | 12/1976 | Clark, III . |
| 4,018,576 | 4/1977 | Lowder et al. . |
| 4,046,150 | 9/1977 | Schwartz et al. . |
| 4,137,906 | 2/1979 | Akiyama et al. . |
| 4,177,815 | 12/1979 | Patel . |
| 4,195,637 | 4/1980 | Grüntzig et al. . |
| 4,273,128 | 6/1981 | Lary . |
| 4,307,722 | 12/1981 | Evans . |
| 4,323,071 | 4/1982 | Simpson et al. . |
| 4,347,846 | 9/1982 | Dormia . |
| 4,445,509 | 5/1984 | Auth . |
| 4,465,072 | 8/1984 | Taheri . |
| 4,572,186 | 2/1986 | Gould et al. . |
| 4,577,631 | 3/1986 | Kreamer . |
| 4,607,618 | 8/1986 | Angelchik . |
| 4,650,466 | 3/1987 | Luther . |
| 4,679,557 | 7/1987 | Opie et al. . |
| 4,696,667 | 9/1987 | Masch . |
| 4,732,154 | 3/1988 | Shiber . |
| 4,771,774 | 9/1988 | Simpson et al. . |
| 4,784,636 | 11/1988 | Rydell . |
| 4,819,634 | 4/1989 | Shiber . |
| 4,838,853 | 6/1989 | Parisi . |
| 4,842,579 | 6/1989 | Shiber . |
| 4,883,458 | 11/1989 | Shiber . |
| 4,885,003 | 12/1989 | Hillstead . |
| 4,886,061 | 12/1989 | Fischell et al. . |
| 4,886,490 | 12/1989 | Shiber . |
| 4,894,051 | 1/1990 | Shiber . |
| 4,895,166 | 1/1990 | Farr et al. . |
| 4,895,560 | 1/1990 | Papantonakos . |
| 4,921,484 | 5/1990 | Hillstead . |
| 4,957,482 | 9/1990 | Shiber . |
| 4,966,604 | 10/1990 | Reiss . |
| 4,979,939 | 12/1990 | Shiber . |
| 4,990,134 | 2/1991 | Auth . |
| 5,002,553 | 3/1991 | Shiber . |
| 5,007,896 | 4/1991 | Shiber . |
| 5,009,659 | 4/1991 | Hamlin et al. . |
| 5,011,488 | 4/1991 | Ginsburg . |
| 5,024,651 | 6/1991 | Shiber . |
| 5,030,201 | 7/1991 | Palestrant . |
| 5,034,001 | 7/1991 | Garrison et al. . |
| 5,041,082 | 8/1991 | Shiber . |
| 5,100,425 | 3/1992 | Fischell et al. . |
| 5,116,350 | 5/1992 | Stevens . |
| 5,135,483 | 8/1992 | Wagner et al. . |
| 5,135,531 | 8/1992 | Shiber . |
| 5,154,724 | 10/1992 | Andrews . |
| 5,176,693 | 1/1993 | Pannek, Jr. . |
| 5,217,474 | 6/1993 | Zacca et al. . |
| 5,224,945 | 7/1993 | Pannek, Jr. . |
| 5,250,060 | 10/1993 | Carbo et al. . |
| 5,314,407 | 5/1994 | Auth et al. . |
| 5,314,438 | 5/1994 | Shturman . |
| 5,490,849 | 2/1996 | Mische et al. . |
| 5,501,694 | 3/1996 | Ressemann et al. . |
| 5,540,707 | 7/1996 | Ressemann et al. . |

FOREIGN PATENT DOCUMENTS

| | | |
|---|---|---|
| 0 355 861 B1 | 10/1989 | European Pat. Off. . |
| 0 533 321 A2 | 3/1993 | European Pat. Off. . |
| BD 867144 | 12/1952 | Germany . |
| 2 020 557 | 11/1979 | United Kingdom . |
| WO 83/03752 | 11/1983 | WIPO . |
| WO 91/17714 | 11/1991 | WIPO . |
| WO 92/03097 | 3/1992 | WIPO . |
| WO 92/03098 | 3/1992 | WIPO . |
| WO 93/01753 | 2/1993 | WIPO . |
| WO 93/01849 | 2/1993 | WIPO . |
| WO 93/19679 | 10/1993 | WIPO . |

OTHER PUBLICATIONS

Percutaneous Aspiration Thromboembolectomy, Interventional Radiology, Jul. 1985, 156:61–66.

Mechanical Spira Embolectomy Catheter, Irvin F. Hawkins, Jr., M.D., et al., Seminars in Interventional Radiology, vol. 2, No. 4, Dec. 1985, pp. 414–418.

PAT–RAT Acc. to "Starck"–Rotational Aspiration Thromboembolectomy, Angiomed.

Percutaneous Embolectomy by Transcatheter Aspiration, Kenneth W. Sniderman, M.D., et al., Radiology, Feb. 1984 150:357–361.

Percutaneous Transluminal Thrombus Aspiration, E. Starck et al., Angiographic Management of Vascular Obstruction, pp. 625–632.

Advantages of Percutaneous Aspiration Thromboembolectomy, E. Starck et al., pp. 241–247.

Mechanical Thrombectomy, S. Murthy Tadavarthy, M.D., Interventional Radiology, vol. 1, Second Edition, pp. 635–664.

Transvenous Removal of Pulmonary Emboli by Vacuum–Cup Catheter Technique, Lazar J. Greenfield, M.D., Journal of Surgical Research, vol. 9, No. 6, Jun. 1969, pp. 347–352.

Balloon Embolectomy Catheter Used Percutaneously, John C. McDermott, M.D., Radiology, vol. 160, No. 1., p. 279. Correspondence and Brief Communication/Calendar of Events, Arch Surg—vol. 120, Jan. 1985, p. 116.

Percutaneous Aspiration Thromboembolectomy (PAT): An Alternative to Surgical Balloon Techniques for Clot Retrieval, William D. Turnipseed, M.D., et al., Journal of Vascular Surgery, vol. 3, No. 3, Mar. 1986, pp. 437–441.

Peripheral Percutaneous Aspiration Thrombectomy and Angioplasty Following Failed Lytic Therapy for Acute Popliteal Artery Occlusion, George Li, M.D., Journal of Interventional Cardiology, vol. 5, No. 3., 1992, pp. 159–162.

The Roto–Drill, A New Instrument for Thromboendarterectomy, Shafiroff et al., 1961, pp. 316–319.

Percutaneous Embolectomy by Transcatheter Aspiration, Kenneth W. Sniderman, M.D. et al., Radiology, vol. 150, No. 2., pp. 357–361.

Percutaneous Aspiration Thromboembolectomy, Erhard E. Starck, M.D. et al., Radiology, vol. 156, No. 1., pp. 61–66.

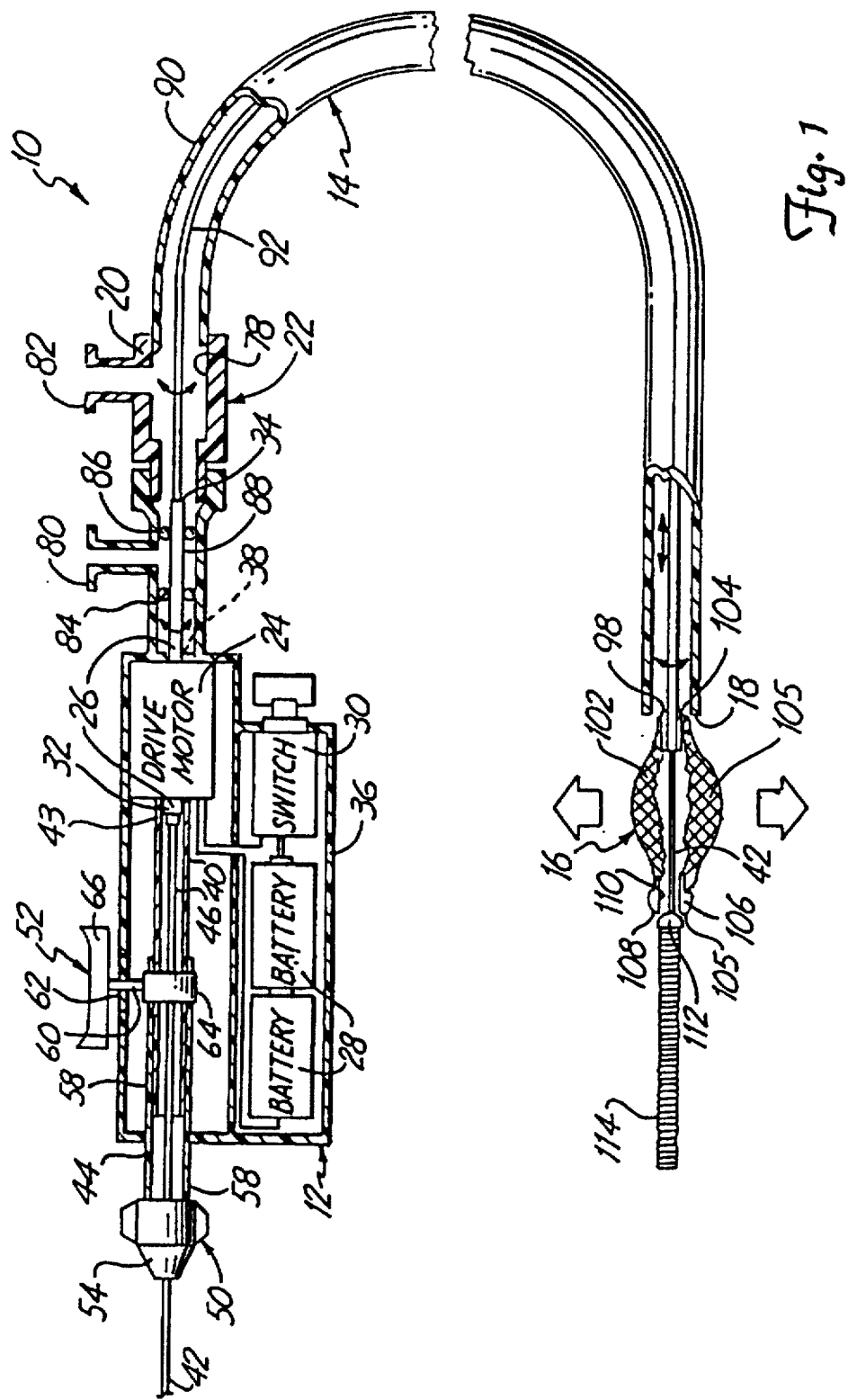

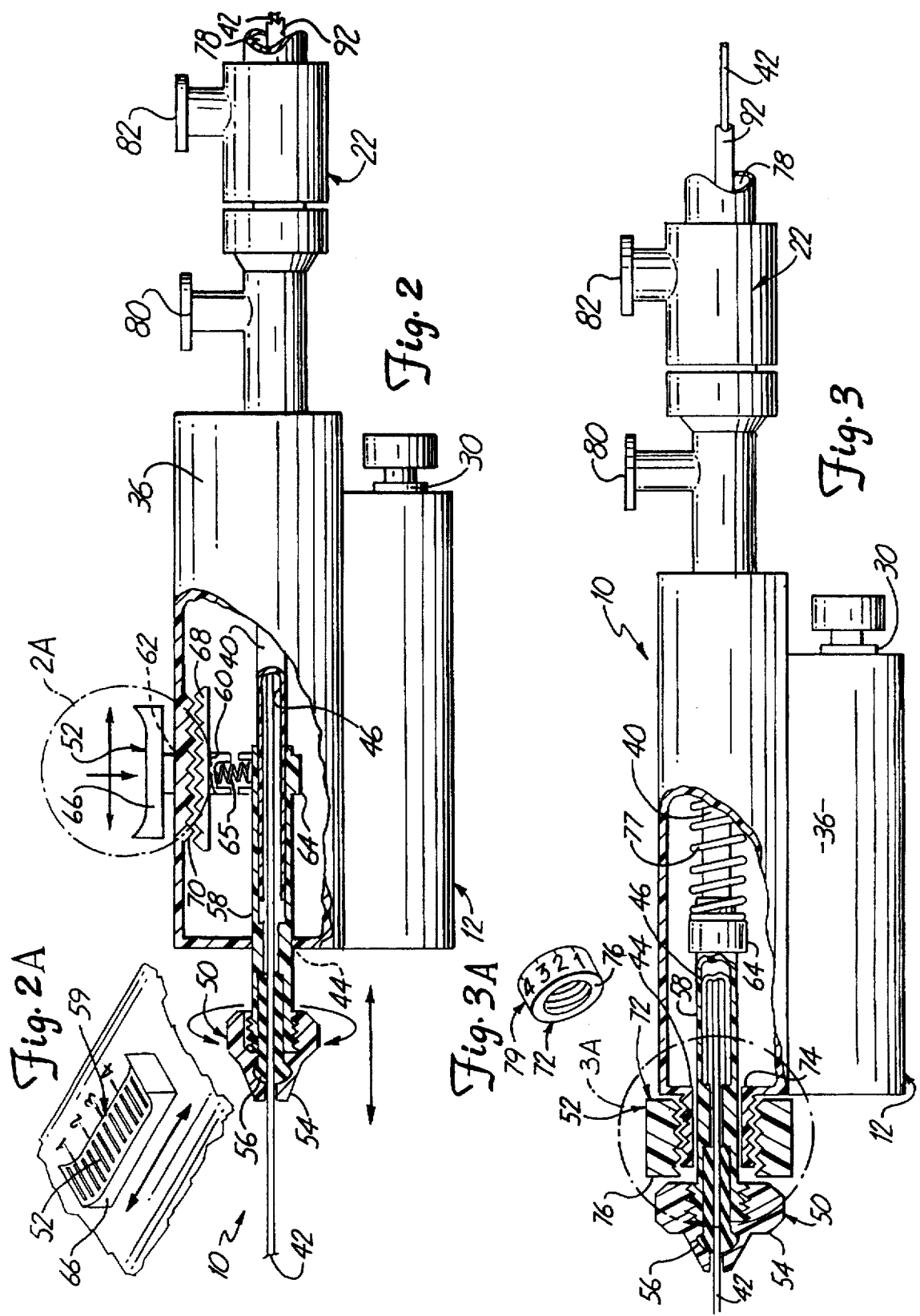

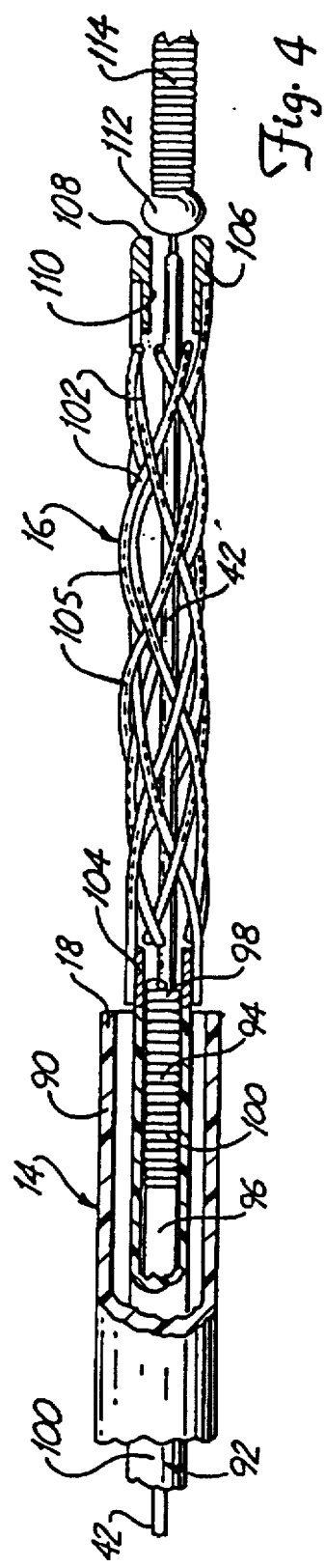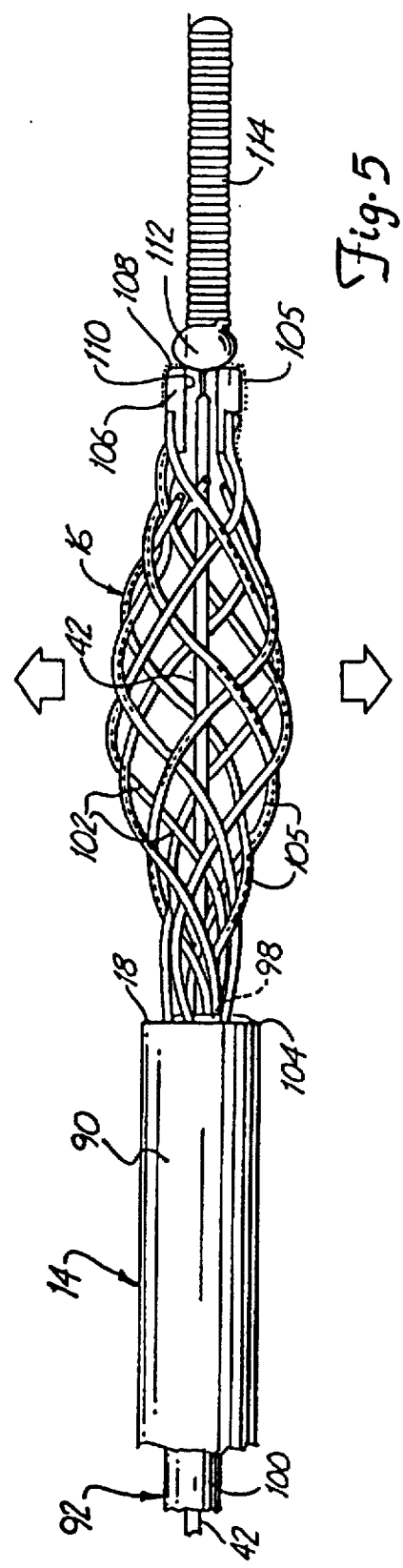

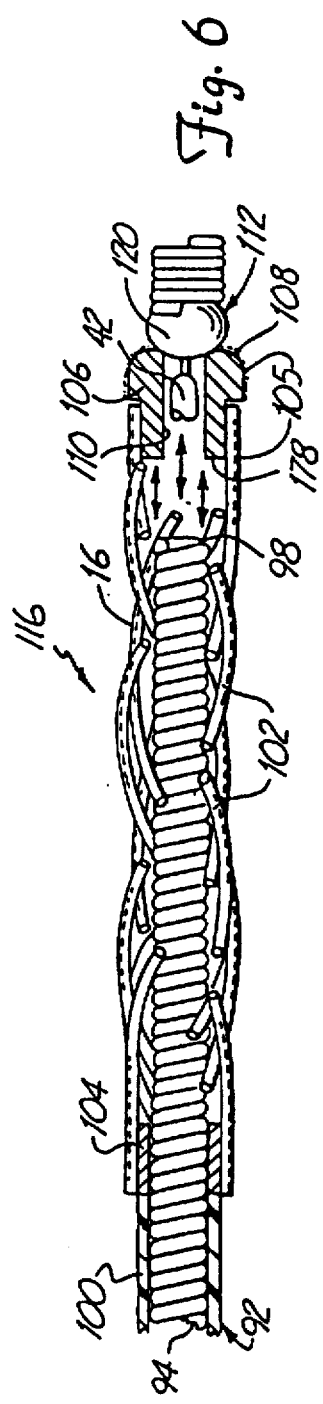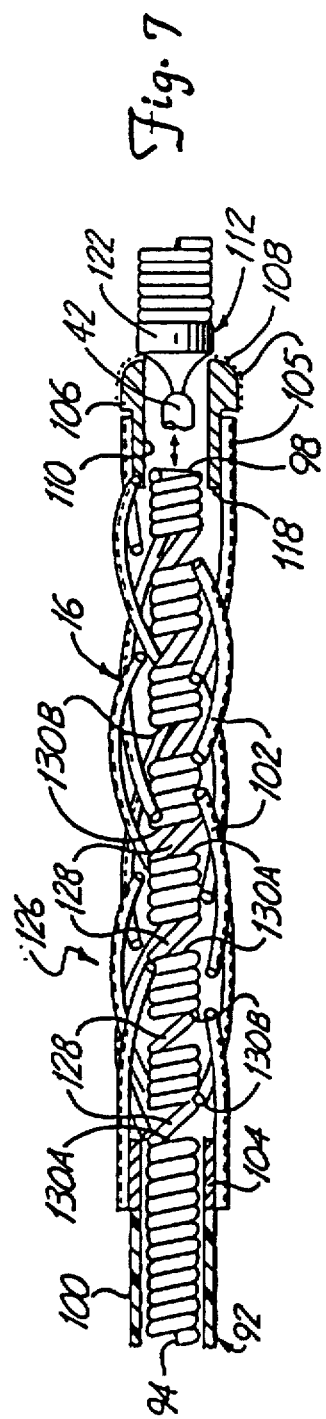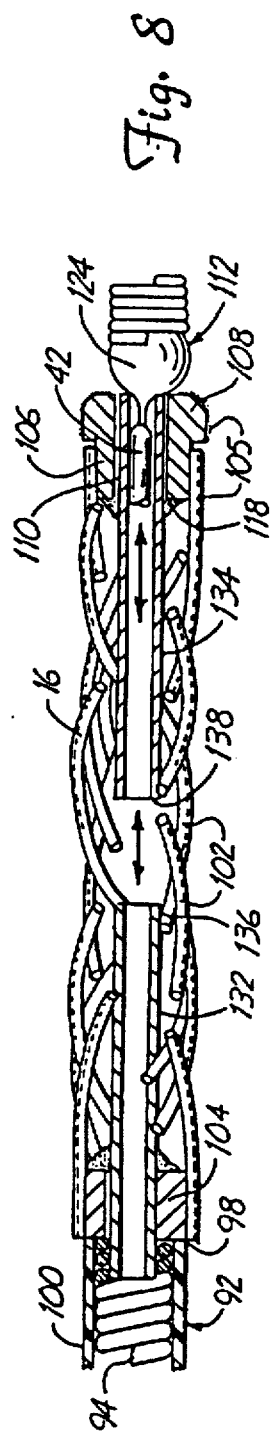

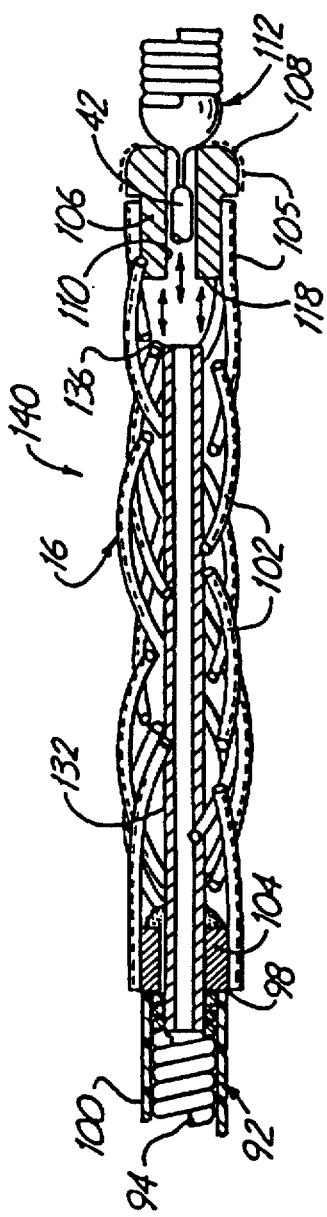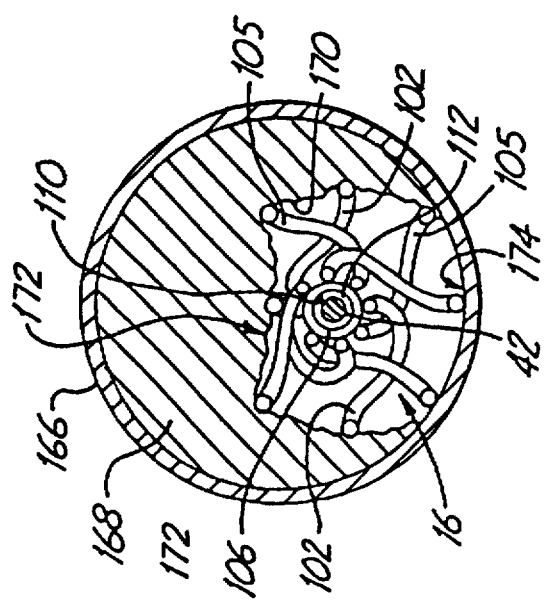

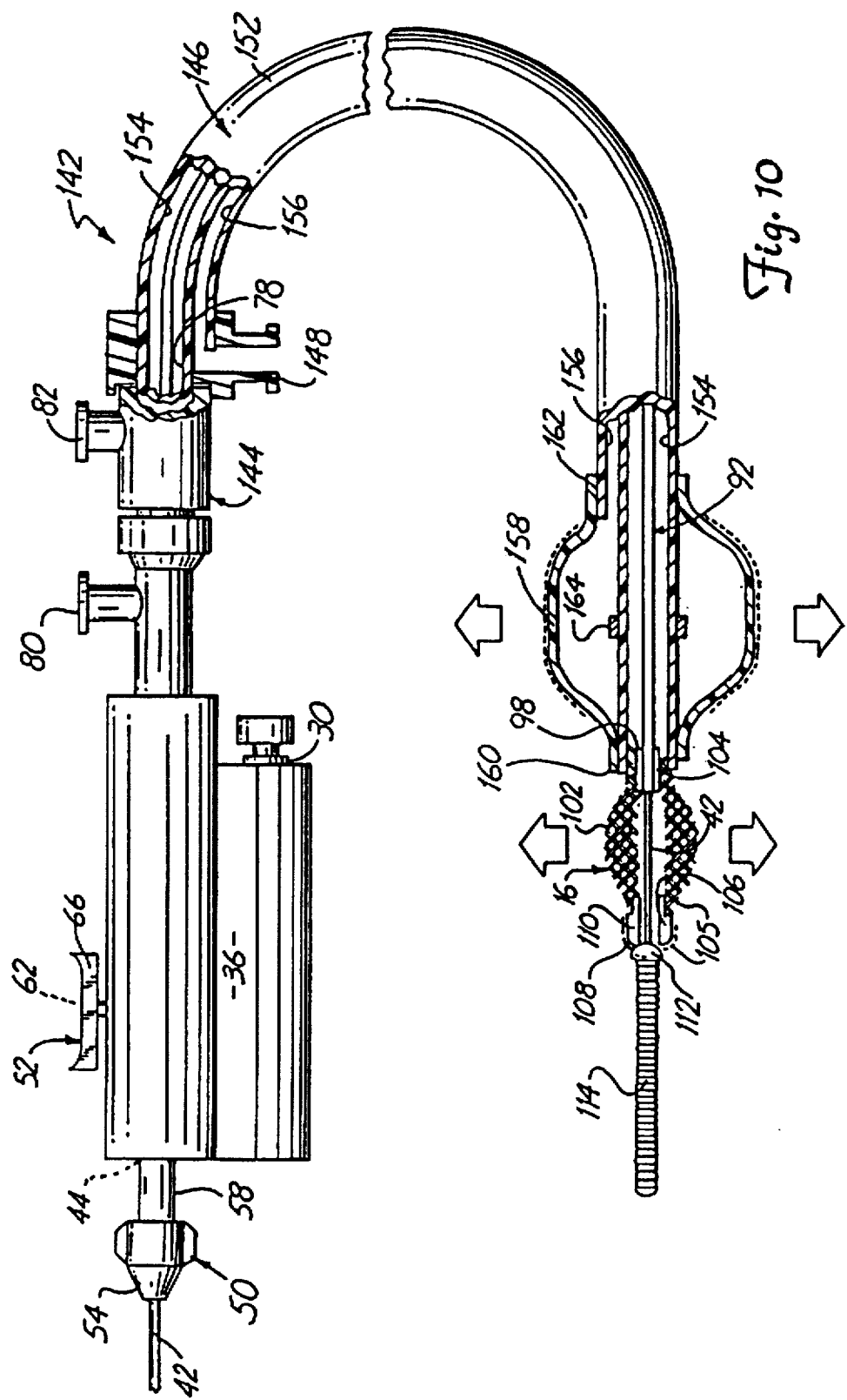

EXPANDABLE INTRAVASCULAR OCCLUSION MATERIAL REMOVAL DEVICES AND METHODS OF USE

"This application is a continuation-in-part of application Ser. No. 08/621,350, filed Mar. 25, 1996, which is a continuation-in-part of application Ser. Nos. 08/206,053, filed Mar. 3, 1994 now U.S. Pat. No. 5,501, 694, and 08/261,813, filed Jun. 17, 1994, now U.S. Pat. No. 5,540, 707, which in turn are continuation-in-part applications of application Ser. No. 08/055,995, filed Apr. 29, 1993, now U.S. Pat. No. 5,490,859, which in turn is a continuation-in-part of application Ser. No. 07/976,199, filed Nov. 13, 1992, now abandoned."

BACKGROUND OF THE INVENTION

The present invention generally relates to novel constructions for intravascular treatment devices useful for removing vascular occlusion material from a vascular occlusion or a vascular lumen. The invention more specifically relates to novel expandable intravascular occlusion material removal devices, as well as to methods of using those devices to treat vascular diseases.

Vascular diseases, such as atherosclerosis and the like, have become quite prevalent in the modern day. These diseases may manifest themselves in a plurality of different ways, thereby often requiring different forms or methods of treatment for curing the adverse effects of the diseases. Vascular diseases, for example, may take the form of deposits or growths in a patient's vasculature which may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies are being developed. While a number of effective invasive therapies are available, it is desirable to develop non-invasive therapies as well. Non-invasive therapies may be less risky than invasive ones, and may be more welcomed by the patient because of the possibility of decreased chances of infection, reduced post-operative pain, and less post-operative rehabilitation. One type of non-invasive therapy for vascular diseases is pharmaceutical in nature. Clot-busting drugs have been employed to help break up blood clots which may be blocking a particular vascular lumen. Other drug therapies are also available. Further non-invasive, intravascular treatments exist that are not only pharmaceutical, but also physically revascularize lumens. Two examples of such intravascular therapies are balloon angioplasty and atherectomy which physically revascularize a portion of a patient's vasculature.

Balloon angioplasty comprises a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and then is inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It is to be noted, however, that this procedure does not remove that matter from the patient's vasculature, but displaces and reforms it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus are not prone or susceptible to angioplastic treatment. Even if angioplasty is successful, thereby revascularizing the vessel and substantially restoring normal blood flow therethrough, there is a chance that the occlusion may recur. Recurrence of an occlusion may require repeated or alternative treatments given at the same intravascular site.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty and/or drug therapies.

One such alternative mechanical treatment method involves removal, not displacement, as is the case with balloon angioplasty, of the material occluding a vascular lumen. Such treatment devices, sometimes referred to as atherectomy devices, use a variety of means, such as lasers, and rotating cutters or ablaters, for example, to remove the occluding material. The rotating cutters may be particularly useful in removing certain vascular occlusions. Since vascular occlusions may have different compositions and morphology or shape, a given removal or cutting element may not be suitable for removal of a certain occlusion. Alternatively, if a patient has multiple occlusions in his vasculature, a given removal element may be suitable for removing only one of the occlusions. Suitability of a particular cutting element may be determined by, for example, its size or shape. Thus, a treating physician may have to use a plurality of different treatment devices to provide the patient with complete treatment. This type of procedure can be quite expensive because multiple pieces of equipment must be used (such intravascular devices are not reusable because they are inserted directly into the blood stream), and may be tedious to perform because multiple pieces of equipment must be navigated through an often-tortuous vascular path to the treatment site.

Given the above-discussed considerations, among others, associated with non-invasive intravascular therapies, it is desirable to provide an intravascular treatment method or device which can address some, if not all of those considerations. The present invention is intended to provide such a device and such a method.

The present invention provides novel intravascular treatment devices having novel vascular occlusion material removing elements which are variably expandable. By varying the expansion of the removal element, a treating physician can change the cutting or removing characteristics of the element. Specifically, by varying element expansion, the removal element can take on a plurality of different shapes and sizes, thereby giving the removal element different cutting or removing configurations and characteristics. Thus, a single vascular occlusion material removal element, constructed according to the teaching of the present invention, may be able to perform tasks which require a plurality of cutting or ablating burrs and devices of the prior art. The invention also provides novel methods of removing vascular occlusions from a vascular surface or an occlusion.

SUMMARY OF THE INVENTION

A general object of the present invention is to provide novel, improved constructions for vascular occlusion material removal elements and associated intravascular devices.

A more specific object of the invention is to provide a novel expandable intravascular device for removing vascular occlusion material from a vascular surface.

Another object of the present invention is to provide a novel intravascular occlusion material removal device which can revascularize vascular lumens to various diameters without the need for multiple pieces of equipment.

A further object of the present invention is to provide an intravascular cutting device or the like having a variable cutting profile or configuration.

An additional object of the invention is to provide a novel vascular occlusion material removal device having an expandable removal element that can be delivered over a guidewire.

A novel intravascular device, constructed according to the teachings of the present invention, for removing vascular occlusion material in a vascular lumen comprises a prime mover and an expandable material removal element insertable intravascularly into the vascular lumen. A hollow drive shaft operatively connects the prime mover to the expandable material removal element for rotating the expandable material removal element intravascularly. A guidewire is insertable through the distal end of the expandable material removal element and the hollow drive shaft, and is shiftable within the drive shaft and the expandable material removal element. The expandable material removal element is expandable responsive to shifting of the guidewire. A material removal element movement control mechanism is operatively connected to the guidewire for positively incrementally shifting the guidewire, and a guidewire lock mechanism is operatively connected between the guidewire and the material removal element movement control mechanism for fixing the guidewire with respect to the material removal element movement control mechanism A number of novel methods, according to the teachings of the present invention, for removing vascular occlusion material are provided. One such method comprises the steps of: providing a vascular occlusion material removal device having an expandable occlusion material removal element, the material removal element comprising a braid having a hollow interior; providing a guidewire; intravascularly navigating the guidewire to the occlusion material; inserting the guidewire into the hollow interior; intravascularly navigating the braid to the occlusion material over the guidewire; shifting the guidewire with respect to the braid to expand the braid; expanding the braid such that the braid bites into occlusion material thereby allowing occlusion material to pass into the hollow interior; and shifting the guidewire with respect to the braid to contract the braid and to capture occlusion material within the hollow interior. The expanded braid can also be rotated intravascularly to remove occlusion material.

BRIEF DESCRIPTION OF THE DRAWINGS

The organization and manner of the structure and operation of the invention, together with further objects and advantages thereof, may best be understood by reference to the following description taken in connection with the accompanying drawings, wherein like reference numerals identify like elements in which:

FIG. 1 is a partially sectioned side elevational view of a novel expandable vascular occlusion material removal device, constructed according to the teachings of the present invention;

FIG. 2 is an enlarged partially sectioned side elevational view of a proximal portion of the occlusion material removal device of FIG. 1;

FIG. 3 is a view, similar to that of FIG. 2, of an alternative embodiment of the proximal portion of the occlusion material removal device of FIG. 1;

FIG. 4 is an enlarged, partially sectioned side elevational view of a distal portion of the occlusion material removal device of FIG. 1 showing an expandable material removal element in a contracted position;

FIG. 5 is a view, similar to that of FIG. 4 illustrating the expandable material removal element in an expanded position;

FIG. 6 is an enlarged, partially sectioned side elevational view of an alternative embodiment of the distal portion of the removal device of FIG. 1;

FIG. 7 is a view, similar to that of FIG. 6, of another embodiment of the distal portion;

FIG. 8 is a view, similar to that of FIG. 7, of an additional embodiment of the distal portion;

FIG. 9 is a view, similar to that of FIG. 8, of yet a further embodiment of the distal portion;

FIG. 10 is a view, similar to that of FIG. 1, of another embodiment of the expandable occlusion material removal device having a dilating member at a distal portion thereof; and FIG. 11 is a sectional view of an expandable occlusion material removal element disposed within an occluded vascular lumen showing the conformity of the removal element to the non-occluded lumen.

DETAILED DESCRIPTION OF PREFERRED EMBODIMENTS

While the invention may be susceptible to embodiment in different forms, there are shown in the drawings, and herein will be described in detail, specific embodiments with the understanding that the present disclosure is to be considered an exemplification of the principles of the invention, and is not intended to limit the invention to that as illustrated and described herein.

The various embodiments of the present invention provide a number of constructions of expandable vascular occlusion material removal devices, intravascular material removal elements, and the like, which can be utilized to perform a plurality of different intravascular treatments, such as atherectomy, thrombectomy, angioplasty and the like. The embodiments of the present invention also provide a plurality of methods for using those devices and their associated vascular occlusion material removal elements for performing intravascular treatments on a patient. It is to be fully recognized that the different teachings of the below-discussed embodiments can be employed separately or in any suitable combination to produce desired results. The embodiments provide, in the form of expandable intravascular removal elements, novel ways of changing cutting or removing profiles, configurations or characteristics of a particular intravascular treatment device while only using a single removal element.

Referring initially to FIG. 1, an expandable intravascular occlusion removal device 10, constructed according to the teachings of the present invention, is illustrated. The removal device 10 generally comprises a drive assembly 12, a catheter assembly 14, and an expandable material removal element 16 located at a distal end 18 of the catheter assembly 14. A proximal end 20 of the catheter assembly 14 is connected to a manifold assembly 22 which forms a connection between the drive assembly 12 and the catheter assembly 14.

The construction of the drive assembly 12 and the manifold assembly 22 are more clearly shown in FIG. 2. The drive assembly 12 generally comprises an electric motor 24 having a hollow, rotatable drive shaft 26, a power source 28, illustrated as a plurality of batteries electrically connected in series, for energizing the motor 24, and a control switch 30 connected electrically between the motor 24 and the power source 28 such that actuation of the control switch 30 allows current to flow between the power source 28 and the motor 24, thereby causing the drive shaft 26 to rotate. In an exemplary embodiment of the invention, the motor 24 is a direct current micro-motor available from Micro Mo Electronics, Inc., series number 2233-04.5S, and the power source 28 is a pair of 3 Volt lithium batteries. The motor 24 can rotate the drive shaft 26 at a speed of about 10,000 revolutions per minute, but it is envisioned that greater speeds, on the order of 100,000 revolutions per minute may be possible with different motors 24. For example, the motor 24 may be similar to the brushless direct current motor available from Transicoil Inc. of Valley Forge, Pa., model number U-222285, which can reach speeds of 100,000 revolutions per minute. By rotating the drive shaft 26 at this speed, more efficient removal of occlusion material may be achieved because the intravascular treatment may take less time. Thus, the removal device 10 can operate at speeds substantially within the range of 0 to 100,000 revolutions per minute. As FIG. 2 shows, the drive shaft 26 extends through the motor 24 with a proximal end 32 thereof projecting from a proximal end of the motor 24, and with a distal end 34 thereof extending out of an aperture 38 located on a distal end of a housing 36 which contains elements of the drive assembly 12. The significance of this structure will become clear later.

An inner hollow tube or sheath 40 is located between an inner, proximal end of the housing 36 and the proximal end of the motor 24 such that the proximal end 32 of the drive shaft 26 extends into the hollow interior of the inner sheath 40. The inner sheath 40 defines a lumen 46 of dimensions sufficient for accepting a medical guidewire 42, made of stainless steel, nitinol, and the like, which can extend from the guidewire lumen 46 within the inner sheath 40, and through an aperture 44 in the proximal end of the housing 36 to the exterior of the housing 36. Because the drive shaft 26 of the motor 24 is hollow, the guidewire 42 can pass through the catheter assembly 14, into the manifold assembly 22 and into the drive shaft 26. A fluid seal 43, such as a diaphragm and the like, is provided at the proximal end 32 of the drive shaft 26 so that fluid within the drive shaft 26 cannot leak into the interior of the housing 36. However, the fluid seal 43 is of appropriate construction to allow the guidewire 42 to extend from the drive shaft 26 into the inner sheath 40.

The distal end 34 of the drive shaft 26 of the motor 24 is fixedly connected to a hollow drive shaft 92 which extends axially through the catheter assembly 14 and is connected to the material removal element 16. In an exemplary embodiment, the drive shaft 92 has an outer diameter of about 0.025". The hollow drive shaft 92 also defines a guidewire lumen, thereby allowing for passage of the guidewire 42 from the material removal element 16 to the exterior of the housing 36. Thus, the removal device 10 is of an over-the-wire construction which can facilitate removing the device 10 from, and replacing the device 10 in the patient because the guidewire 42 can remain within the patient. Comparatively, some prior art devices require removal of the guidewire along with the device, thereby necessitating additional intravascular navigation not only of the device, but also of the guidewire to replace the device adjacent the occlusion material to be removed. In addition, the presence of the guidewire 42 facilitates intravascular navigation of the removal device 10, because the device 10 can be delivered over the guidewire 42, which is an improvement over some expandable intravascular devices.

The guidewire 42 is also axially shiftable with respect to the drive assembly 12 and the catheter assembly 14 so that shifting of the guidewire 42 induces corresponding movement of the material removal element 16 between a contracted position (FIG. 4) and an expanded position (FIG. 5). This operation will be discussed in greater detail hereinbelow. The guidewire 42 must have sufficient strength to transmit force to the material removal element 16 to cause movement between the contracted and expanded positions. This is an important distinction from some prior art devices which require a mechanism in addition to a medical guidewire to expand an element intravascularly. Thus, the expandable intravascular occlusion material removal device 10 is of a construction substantially simpler than some of the prior art devices. A variable length of the guidewire 42 can be shifted distally of the removal element 16 for facilitating intravascular navigation of the removal device 10. In an exemplary embodiment of the removal device 10, the guidewire 42 has an outer diameter measuring substantially within the range of 0.010" to 0.014".

Because axial shifting of the guidewire 42 causes expansion or contraction of the material removal element 16, the drive assembly 12 includes structures for providing a treating physician with positive control over axial movement of the guidewire 42. Specifically, as shown in FIG. 2, the drive assembly 12 includes a guidewire lock mechanism 50 and a material removal element expansion control mechanism 52, both of which serve to positively control expansion or contraction of the material removal element 16 by controlling axial shifting of the guidewire 42. The guidewire lock mechanism 50 holds the guidewire 42 fixed with respect to itself and to the control mechanism 52 which allows a treating physician to positively axially shift the guidewire 42 and the guidewire lock mechanism 50 by actuation of the expansion control mechanism 52, as will be discussed in greater detail later.

The guidewire lock mechanism 50 is located at a proximal end of the housing 36 adjacent the aperture 44. The guidewire lock mechanism 50 may function substantially similarly to a pin vise, and comprises a wire lock knob 54 and an inner collet 56, shown in section in FIG. 2, through which the guidewire 42 passes. The wire lock knob 54 and the inner collect 56 are disposed at a proximal end of an outer hollow tube or sheath 58 which also passes through the aperture 44 into the interior of the housing 36. The outer sheath 58 is of dimensions sufficient to accept the guidewire 42 and also the inner sheath 40. The outer sheath 58 is axially shiftable with respect to the inner sheath 40, and slides along an outer surface of the inner sheath 40, which remains fixed within the housing 36, responsive to actuation of the expansion control mechanism 52, as will be discussed below.

A portion of the inner collet 56 extends into the interior of the outer sheath 58 where that portion can engage an outer diameter surface of the guidewire 42. The wire lock knob 54 is rotatable with respect to the inner collet 56 and the outer sheath 58, and is threaded variably onto the proximal end of the outer sheath 58. Thus, as the wire lock knob 54 is appropriately rotated with respect to the inner collet 56 and the outer sheath 58, the wire lock knob 54 moves distally along the outer sheath 58 by means of the threaded engagement therebetween, which forces the inner collet 56 to engage the outer surface of the guidewire 42. The wire lock knob 54 is rotated on the outer sheath 58 sufficiently to compress the inner collet 56 against the guidewire 42 such that the guidewire 42 is fixed with respect to the guidewire lock mechanism 50 and the outer sheath 58. However, the outer sheath 58 is axially shiftable with respect to the inner sheath 40, the motor 24 and the drive shaft 26 responsive to actuation of the expansion control mechanism 52. Thus, the guidewire 42 is also positively shiftable responsive to movement of the control mechanism 52. Proper application of the guidewire lock mechanism 50 to the guidewire 42 allows a physician to positively vary expansion and/or contraction of the expandable material removal element 16. To release the guidewire 42 from the grip of the inner collet 56 and the wire lock mechanism 50, the wire lock knob 54 is rotated in an opposite direction, thereby allowing a portion of the inner collet 56 to move out of the outer sheath 58, and out of engagement with the outer surface of the guidewire 42.

The material removal element expansion control mechanism 52 is operatively connected to the outer sheath 58 such that actuation of the control mechanism 52 causes conjoint motion of the outer sheath 58 and the guidewire 42, which causes expansion and/or contraction of the material removal element 16 (assuming that the wire lock mechanism 50 holds the guidewire 42 fixed with respect to the control mechanism 52 and the outer sheath 58). Specifically, the material removal element expansion control mechanism 52 comprises a shaft 60 extending substantially perpendicularly from the inner sheath 40 and the outer sheath 58 through an elongate slot 62 in the housing 36. One end of the shaft 60 is connected to a shoulder portion 64 located adjacent a distal end of the outer sheath 58 by a compressible spring 65. The spring 65 biases the shaft 60 away from the outer sheath 58. An opposite end of the shaft 60 extends out of the housing 36 through the slot 62 where it is connected to a thumb pad 66. The thumb pad 66 is configured for facilitating application of a force from a treating physician's thumb to induce axial shifting of the guidewire 42, and thus, corresponding expansion and/or contraction of the expandable material removal element 16.

Means is provided within the housing 36 to facilitate positive shifting of the guidewire 42, and also positive expansion and/or contraction of the expandable material removal element 16. Specifically, in the illustrated embodiment, a first set of teeth 68 is attached to the shaft 60 such that the teeth 68 extend perpendicularly with respect to an axis of elongation of the shaft 60 and substantially parallel with respect to an adjacent portion of the housing 36. Because the shaft 60 can move against the spring 65 under the influence of forces applied to the thumb pad 66, the first set of teeth 68 are also movable in corresponding fashion. A second set of teeth 70 depend from the interior surface of the housing 36 adjacent the slot 62 such that the first set of teeth 68 are interengagable with the second set of teeth 70. The second set of teeth 70 are fixed with respect to the housing 36 such that, when the teeth 68 and 70 are interengaged, the outer sheath 58 is fixed with respect to the housing 36. This prevents axial shifting of the guidewire 42 with respect to the drive assembly 12, the catheter assembly 14, and the removal element 16 if the guidewire lock mechanism 50 is applied.

The structure of the guidewire lock mechanism 50 and the material removal element expansion control mechanism 52 may be more readily understood with reference to the following discussion of the operation thereof. The guidewire 42 is disposed through the drive shaft 26, the motor 24, the inner sheath 40, the outer sheath 58, the inner collet 56 and the wire lock knob 54. The wire lock knob 54 is rotated with respect to the outer sheath 58 such that threads on the lock knob 54 and the outer sheath 58 cooperate to cause distally directed movement of the lock knob 54 with respect to the outer sheath 58. Distally directed movement of the lock knob 54 forces the inner collet 56 progressively further into the interior of the outer sheath 58. As the inner collet 56 moves into the outer sheath 58, a portion of the inner collet 56 within the outer sheath 58 engages an outer surface of the guidewire 42. The wire lock knob 54 is rotated on the outer sheath 58 so that the portion of the inner collet 56 engages the outer surface of the guidewire 42 with sufficient force to hold the guidewire 42 fixed with respect to the outer sheath 58 and the guidewire lock mechanism 50. The guidewire 42, the guidewire lock mechanism 50 and the outer sheath 58 now move conjointly.

A treating physician applies an appropriate force to the thumb pad 66, thereby causing movement of the shaft 60 towards the shoulder portion 64 of the outer sheath 58 and compressing the spring 65 between an end of the shaft 60 and the shoulder portion 64 of the outer sheath 58. Sufficient movement of the shaft 60 towards the shoulder portion 64 and sufficient compression of the spring 65 disengages the teeth 68 from the teeth 70 because the teeth 68 move conjointly with the shaft 60 while the teeth 70 remain fixed. The treating physician can now apply forces to the thumb pad 66 to conjointly axially shift the guidewire 42, the outer sheath 58, the guidewire lock mechanism 50 and the material removal element expansion control mechanism 52.

Specifically, the treating physician can apply forces to the thumb pad 66 to move or shift the guidewire 42 and the outer sheath 58 proximally rearwardly. This movement, as will be discussed in greater detail later, causes expansion of the material removal element 16. As these forces are applied to the thumb pad 66, those forces are transmitted to the shoulder portion 64 of the outer sheath 58. The outer sheath 58 slides proximally along the outer surface of the inner sheath 40 towards the aperture 44 in the housing 36. The range of sliding motion of the outer sheath 58 along the inner sheath 40 is limited by engagement of a proximal end of the teeth 68 with the adjacent interior surface of the housing 36, as well as by the dimensions of the elongate slot 62 in which a portion of the shaft 60 moves conjointly with the outer sheath 58.

The degree of material removal element 16 expansion is directly proportional to the length of axial shifting of the guidewire 42 and the outer sheath 58 proximally. Thus, the degree of material removal element 16 expansion and/or contraction can be measured by suitable scaling means 59 or 79 disposed on the housing 36 adjacent the elongate slot 62. When a desired degree of material removal element 16 expansion has been achieved, the thumb pad 66 can be released. The spring 65 now expands and forces the teeth 68 into engagement with the teeth 70. Interengagement of the teeth 68 and 70 positively locks the axial position of the guidewire 42, and thus, also the expanded position of the material removal element 16. Because a plurality of teeth 68 and 70 are provided, the material removal element expansion control mechanism 52 allows for positively controlled, incremental expansion of the material removal element 16. To contract the expandable material removal element 16, the above-discussed steps are repeated, but this time, the treating physician moves the thumb pad 66 and the guidewire 42 distally.

An alternative embodiment of the material removal element expansion control mechanism 52 is illustrated in FIG. 3. It is to be noted that the construction of this embodiment is substantially similar to that illustrated in FIGS. 1 and 2, except for the differences noted hereinbelow, hence the like reference numerals for similar structures. The guidewire lock mechanism 50 of the embodiment of FIG. 2 is the same as that of the embodiment of FIG. 3.

Specifically, in the embodiment of FIG. 3, the material removal element expansion control mechanism 52 comprises an expansion knob 72 and a threaded hub 74. The threaded hub 74 extends from and is fixed to a proximal end of the housing 36 and surrounds the aperture 44 in the housing 36 and the outer sheath 58. The expansion knob 72 has internal threads matable with the threads on the threaded hub 74, and is disposed on the hub 74 such that the knob 72 surrounds the hub 74. The expansion knob 72 is rotatable on the threaded hub 74, and the threads thereon cooperate so that rotation of the expansion knob 72 on the threaded hub 74 causes the expansion knob 72 to move proximally or distally with respect to the hub 74, depending upon the direction of rotation. Distal movement of the expansion knob 72 causes contraction of the material removal element 16 and proximal movement of the expansion knob 72 causes expansion of the material removal element 16.

To expand the material removal element 16, the expansion knob 72 is rotated such that the knob 72 moves proximally on the threaded hub 74 so that a proximal end 76 of the expansion knob 72 contacts a distal end of the wire lock knob 54. Further proximal motion of the expansion knob 72 forces the wire lock knob 54 to shift proximally with respect to the drive assembly 12, thereby shifting the guidewire 42 proximally as well. The outer sheath 58 conjointly slides proximally along the outer surface of the inner sheath 40, as discussed above. Proximal movement of the expansion knob 72 on the threaded hub 74 is positively limited, thereby limiting the maximum size of the expandable material removal element 16. Specifically, upon sufficient rotation and proximal movement of the expansion knob 72, a proximal end of the shoulder portion 64 engages an interior proximal side of the housing 36.

The expandable material removal element 16 can be contracted by reversing the direction of rotation of the expansion knob 72. To facilitate return of the material removal element 16 from the expanded position to the contracted position, a coiled spring 77 may be disposed between the shoulder portion 64 and the proximal end of the motor 24, as shown in FIG. 3, or, alternatively, disposed between the shoulder portion 64 and the proximal end of the housing 36. The spring 77 relaxes as the expansion knob 72 moves distally on the threaded hub 74. Relaxation of the spring 77 moves the outer sheath 58, the wire lock knob 54 and the guidewire 42 proximally with respect to the drive assembly 12. Suitable scaling means 59 or 79 can be provided on the expansion knob 72 and/or the housing 36 for providing a treating physician with a positive indication of the degree of expansion and/or contraction of the expandable material removal element 16.

The construction of the manifold assembly 22 is illustrated in FIGS. 1 through 3. The manifold assembly 22 connects the drive assembly 12 to the catheter assembly 16. The manifold assembly 22 generally comprises a main lumen 78 which extends from a distal end of the housing 36 to the proximal end 20 of the catheter assembly 14, and has at least two ports 80 and 82, accessible from the exterior of the manifold assembly 22, which communicate with the main lumen 78. The hollow drive shaft 26 of the motor 24 extends through the aperture 38 in the housing 36 and into the main lumen 78. The drive shaft 26 has a lumen therein of dimensions sufficient for accepting the guidewire 42 so that the guidewire 42 can also extend into the main lumen 78 within the drive shaft 26.

In the illustrated embodiment, the drive shaft 26 extends into the main lumen 78 a distance sufficient to locate the distal end 34 of the drive shaft 26 distally of the port 80. A pair of fluid seals 84 and 86 are provided within the main lumen 78 on opposite sides of the port 80. The fluid seals 84 and 86 extend from the main lumen 78 to an outer surface of the drive shaft 26 and form a fluid-tight seal around a portion of the drive shaft 26 therebetween. A longitudinal aperture 88 is located on the drive shaft 26 between the fluid seals 84 and 86 for allowing fluid to pass into the hollow interior of the drive shaft 26. This construction allows the port 80 to be dedicated to infusion of fluids into the drive shaft 26. This infused fluid can provide for increased lubrication between the outer surface of the guidewire 42 and the inner surface of the drive shaft 26, which may be beneficial during operation of the motor 24, and for allowing irrigation of an intravascular treatment site, which may be necessary to maintain a fluid balance within a vascular lumen if aspiration techniques also used. Accordingly, the port 80 is connectable to a suitable fluid source, not shown, but well known in the art. The port 82 can be utilized for infusion of fluids, such as contrast media, saline, a drug therapy, and the like, into the patient, and for aspiration of the intravascular treatment site. The fluid seals 84 and 86 provide for this independent operation of the ports 80 and 82, and also insure that fluids introduced into the main lumen 78 will not reach the motor 24. To insure delivery of the fluids for infusion or negative pressures for aspiration, the port 82 communicates with a catheter sheath 90 connected to the distal end of the manifold assembly 22. The catheter sheath 90 is of well known construction, and can be made from polyethylene, TEFLON®, a fluoropolymer and the like. In an exemplary embodiment, the catheter sheath 90 can have an axial length of about 133 cm and an outer diameter of about 0.060", thereby enabling it to be inserted into a 7 French guide catheter. The proximal end of the catheter sheath 90 defines the proximal end 20 of the catheter assembly 14.

The distal end 34 of the hollow drive shaft 26 is fixedly attached to another hollow drive shaft 92, which extends through the catheter sheath 90 of the catheter assembly 14, so that the drive shafts 24 and 92 rotate conjointly. The novel construction of the drive shaft 92 is illustrated in FIGS. 4 and 5. Specifically, the drive shaft 92 comprises an inner coil 94, preferably formed from a plurality of intertwined strands of a wire composed of a suitable metal, such as stainless steel or nitinol, wound in a predetermined direction such that the coil 94 expands radially upon rotation of the drive shaft 92. This maintains or increases the clearance between the outer surface of the guidewire 42 and the inner surface of the coil 94. In order to limit radial and axial expansion of the inner coil 94, a wire braid 96, formed from a metal such as stainless steel, nitinol or the like, is applied over a portion of the outer diameter surface of the coil 94. Wires forming the inner coil 94 and the braid 96 can have a rounded or flattened configuration.

An end of the braid 96 is applied over the outer diameter surface of the coil 94 and attached by suitable means, such as solder, braze, and the like, to a proximal end of the inner coil 94. The braid 96 is then stretched axially or tensioned along the length of the inner coil 94, thereby closely confining radial expansion of the individual windings of the inner coil 94. Once stretched, an end of the braid 96 is attached to a portion of the inner coil 94 preferably offset proximally of a distal end 98 of the inner coil 94. This, in the illustrated embodiment, leaves a number of distal-most windings of the inner coil 94 uncovered by the braid 96, however, it is to be understood that the braid 96 can extend along the entire axial length of the coil 94 or may be entirely eliminated without departing from the scope of the invention.

Tensioning the braid 96 over the outer diameter surface of the inner coil 94 limits the radial expansion of the coil 94 during operation of the motor 24. In addition, by covering the proximal portion of the inner coil 94 with the braid 96, the drive shaft 92 has an increased torque rigidity as compared to the coil 94 alone. Torque transfer to the expandable material removal element 16 is correspondingly increased, and the distal end 98 of the inner coil 94 is more responsive to proximally applied torques. Furthermore, by leaving a distal-most portion of the coil 94 uncovered by the braid 96, that portion is rather flexible and has increased tractability, thereby making it easier to torque the distal end 98 through tight curves within a patient's vasculature. To further improve tractability, as well as to reduce friction between the outer surface of the drive shaft 92 and the inner surface of the catheter sheath 90, a lubricous coating 100, comprised of TEFLON® and the like, is applied to the outer surface of the drive shaft 92. The lubricous coating 100 may be provided in the form of a sheath of TEFLON® which shrinks upon application of heat. In this manner, the lubricous coating 100 can reduce friction between the drive shaft 92 and the coating 100, provide the drive shaft 92 with increased torsional rigidity, limit radial expansion of the drive shaft 92, and form a fluid-tight lumen through the drive shaft 92. The lubricous coating 100 can also insure proper aspiration through the catheter sheath 90 by minimizing friction between the drive shaft 92 and occlusion material aspirated into the catheter sheath 90. Also, as shown in FIGS. 1, 4 and 5, the catheter sheath 90 terminates at a location offset proximally of the distal end 98 of the drive shaft 92 and a proximal end of the material removal element 16. This provides for proper irrigation and aspiration of an intravascular treatment site because the irrigation site is located distally of the aspiration site.

The distal end 98 of the inner coil 94 is fixedly attached to the expandable material removal element 16 so that the drive shaft 92 and the material removal element 16 rotate conjointly. The material removal element 16 generally comprises a plurality, preferably 8 or 16, of braided wires 102. The wires 102 themselves preferably have a substantially round configuration defining an outer diameter of about 0.002" to 0.006", although flat, square, or triangular configurations can also be used. In an exemplary embodiment, the wires 102 define a removal element 16 having an axial length of about 1.5 cm. and an outer diameter of about 1.25 mm in the contracted position. In the fully expanded position, the removal element 16 can define an outer diameter measuring substantially within the range of 2.5 to 4.0 mm.

The outer surfaces of the wires 102 may be sharpened, etched or coated with an abrasive 105, such as a diamond grit and the like, to improve the removing or cutting characteristics of the material removal element 16. Preferably, a diamond grit having a grit size substantially within the range of 5 to 100 microns is electroplated onto the wires 102 in substantially uniform manner, however, the grit may be asymmetrically deposited on the wires 102 if desired. The electroplating process may be substantially similar to that disclosed in U.S. Pat. Nos. 3,894,673 and 4,018,576. The wires 102 are preferably made from a super elastic or shape memory metal alloy, such as nitinol and the like, which allows the wires 102 to recover strains greater than those recoverable by other metals. This increased strain recovery allows the wires 102 to resist permanent deformation during repeated expansions and contractions as well as during contact with vascular occlusion material. The use of superelastic alloys for the wires 102 facilitates return of the material removal element 16 to its original low profile, contracted condition, which also makes intravascular navigation of the material removal element 16 easier and insures that vascular occlusion material disposed within the material removal element 16 will be retained therein. In a preferred construction, the expandable material removal element 16 and the catheter assembly 14 as a whole have a sufficiently low profile to allow insertion of the catheter assembly 14 and the material removal element 16 through a conventional 7 French guide catheter.

A proximal annulus 104 is attached to the distal end 98 of the inner coil 94 by suitable means, such as an adhesive, solder, braze or a weld, and the proximal ends of the braided wires 102 are attached to the outer surface of the proximal annulus 104 by similar means. Thus, the braided wires 102 comprising the material removal element 16 rotate conjointly with the drive shafts 26 and 92 and the proximal annulus 104 under the influence of forces generated by the motor 24. The distal ends of the wires 102 are attached to a distal annulus 106, preferably made of a metal. The proximal annulus 104 and the distal annulus 106 are rendered radioscopically visible when the wires 102 are attached thereto. The distal annulus 106 is provided with a substantially frusto-conical or tapered cutting surface 108 located distally of the point of attachment of the wires 102 so that the distal annulus 106 can act as a cutting burr, which may be useful in creating a pilot hole through tight, constricted vascular occlusions. The cutting surface 108 may also be coated with an abrasive 105, such as the diamond grit disclosed earlier. It is also envisioned that the cutting surface 108 may have an auger-like configuration.

The braided wires 102 of the material removal element 16 define a hollow interior which can be used to ingest or capture vascular occlusion material, as will be discussed in greater detail below. Abrasive 105 on the portions of the wires 102 facing the hollow interior may facilitate retention of the captured occlusion material within the hollow interior. In addition, the dimensions of the hollow interior are sufficient to accept a distal portion of the guidewire 42. Specifically, an aperture 110 is provided in the distal annulus 106 so that the guidewire 42 can be inserted therethrough and into the hollow interior of the material removal element 16. From there, the guidewire 42 can be inserted through the proximal annulus 104 into the hollow drive shaft 92, the drive shaft 26, the motor 24, and through the inner sheath 40, the outer sheath 58, and the guidewire lock mechanism 50. To traverse this distance, the guidewire 42 may be of a length suitable for facilitating removal and replacement of the device 10 within a patient, or may be extendable, and may be coated with a lubricous substance, such as TEFLON® or a TEFLON® loaded nickel plating, to facilitate force transfer from the guidewire 42 to the distal end of the material removal element 16. The removal device 10 can also be exchanged intravascularly according to the methods disclosed in the copending U.S. patent application of Mazzola et al., Ser. No. 07/789,183, filed on Nov. 8, 1991. That application is assigned to the assignee of the present invention, and the disclosure thereof is incorporated herein by reference.

A distal end of the guidewire 42 includes a bearing surface 112, which can have several embodiments (FIGS. 6 through 9), which is fixedly attached to the guidewire 42. For example, the bearing surface 112 may be a short tube, a bearing or a bead 120 (FIG. 6) slipped onto the guidewire 42 having a smooth, low friction surface, a braze or solder fillet 122 (FIG. 7), or may be a centerless ground bump 124 (FIG. 8) on the guidewire 42. The bearing surface 112 is located at a proximal end of a radiopaque coil 114 which defines a distal-most end of the guidewire 42. The coil 114 can be made from platinum or other suitable substance, and, in an exemplary embodiment, has an axial length of about 3 cm and an outer diameter or about 0.014". The dimensions of the bearing surface 112 are larger than the corresponding dimensions of the aperture 110 in the annulus 106 so that the bearing surface 112 butts up against a distal end of the annulus 106, the significance of which will become more clear later. For example, the bearing surface 112 may define an outer diameter of about 0.016" and the aperture 110 may define an inner diameter of about 0.010" to 0.014". As stated above, the outer diameter surface of the guidewire 42 may be coated with a lubricous coating, such as TEFLON®, a fluoropolymer-loaded metallic coating, a silicone dispersion, and the like, to minimize friction between the guidewire 42 and the drive shafts 26 and 92. This may be desirable because the guidewire 42 remains within the drive shafts 26 and 92 and is secured against axial movement by the wire lock mechanism 50 during operation of the occlusion material removal device 10.

With the basic structure of the occlusion material removal device 10 being thusly disclosed, a greater appreciation of the construction and benefits of the expandable material removal element 16 of the device 10 may be gained from the following discussion of the operation of the device 10. It is to be noted that this discussion is provided for illustrative purposes only, and is not intended to limit the scope of the present invention.

The guidewire 42 is inserted intravascularly into the patient and navigated to the intravascular treatment site. If possible, the radiopaque coil 114 may be located distally of vascular occlusion material to be removed. A proximal end of the guidewire 42 is inserted through the distal annulus 106, and is guided through the more proximal portions of the removal device 10 until the distal end of the distal annulus 106 is proximate to the proximal end of the bearing surface 112 within the patient's vasculature. This procedure can be used if the guidewire 42 has sufficient length, i.e. is of exchange length. For shorter guidewires 42, the guidewire 42 can be pre-loaded into the removal element 16, and then the guidewire 42 and the element 16 can be conjointly inserted into the patient's vasculature. Sufficient length of the guidewire 42 can be positioned distally of the removal element 16 to facilitate intravascular navigation thereof.

The material removal element 16 is inserted into the patient's vasculature over the guidewire 42 while in the contracted position illustrated in FIG. 4. In a preferred method of use, the removal device 10 is inserted into the patient's vasculature through a guide catheter or an introducer sheath in common fashion. If such a guide is used, then a fluid seal may be provided between the guide catheter and the device 10 to limit blood loss from the patient due to axial shifting of the device 10 with respect to the guide catheter. Thus, back flow of blood or other bodily fluids through a lumen between the guide catheter and the removal device 10 can be limited.

As shown, the axial distance between the distal end 98 of the inner coil 94 and the proximal end of the bearing surface 112 can be sufficient to allow the braided wires 102 comprising the material removal element 16 to completely axially relax or expand, thereby causing the material removal element 16 to contract radially. The proximal end of the bearing surface 112 may not contact the distal end of the distal annulus 106 when the material removal element 16 is in this contracted position. When in the contracted position, the material removal element 16 defines a low profile and an outer diameter slightly larger than the outer diameter of the drive shaft 92. This low profile facilitates intravascular navigation of the material removal element 16.

The removal element 16 is positioned adjacent the occlusion material to be removed. With some embodiments, the coil 114 of the guidewire 42 may have to be located across the occlusion, but it is envisioned that other embodiments may not require this. If the treating physician wishes to shift the material removal element 16 towards the expanded condition illustrated in FIG. 5, then the physician moves the guidewire 42 proximally as described above with reference to the guidewire lock mechanism 50 and the material removal element expansion control mechanism 52. As the treating physician moves the guidewire 42 proximally, the length of the guidewire 42 disposed within the patient's vascular system is reduced. Correspondingly, the axial distance between the bearing surface 112 and the distal annulus 106 decreases until the proximal end of the bearing surface 112 engages the distal end of the distal annulus 106. The guidewire 42 is moved progressively proximally and the axial distance between the distal annulus 106 and the distal end 98 of the inner coil 94 decreases. The braided wires 102 comprising the expandable material removal element 16 are axially compressed, thereby causing the material removal element 16 to expand radially.

Once the material removal element 16 is expanded to the desired degree, which can be positively verified by checking the scaling means 59 or 79 on the drive assembly 12, the thumb pad 66 of the material removal element expansion control mechanism 52 is released and now maintains the expanded position of the material removal element 16. If the physician wishes to radially contract the material removal element 16, then he moves the guidewire 42 distally, as described hereinabove. By suitable manipulation of the guidewire 42, the guidewire lock mechanism 50, and the material removal element expansion control mechanism 52, the material removal element 16 can take on a number of different configurations and sizes, thereby changing the cutting profiles or characteristics of the material removal element 16 without having to remove the material removal element 16 from the patient's vasculature. This can provide the treating physician with greater flexibility in performing intravascular treatments, and may possibly reduce the cost of an intravascular procedure because multiple pieces of equipment need not be used.

While an expandable intravascular removal element is highly desirable for the reasons discussed earlier, it is important that the maximum size of these intravascular cutters be limited. It is important that the expandable removal elements not be over-expanded. While some means for positively limiting radial expansion of the expandable intravascular removal element 16 have been detailed hereinabove, it may be desirable to provide additional safety mechanisms. For instance, it is to be noted that the expansion of the material removal element 16 shown in FIGS. 1, 4, and 5 is limited by contact between a proximal end 118 of the distal annulus 106 and the distal end 98 of the inner coil 94. The embodiments of the invention illustrated in FIGS. 6 through 9 provide novel constructions of removal element expansion limiting means which are included within the expandable elements 16 themselves. In addition, these Figures show some alternative constructions for the bearing surface 112, as indicated earlier.

In the construction 116 of FIG. 6, the distal end 98 of the inner coil 94 extends through and distally of the proximal annulus 104 and into the hollow interior of the material removal element 16 defined by the braided wires 102. This is the currently preferred embodiment of the material removal element radial expansion limiting means. The distal end 98 of the inner coil 94 extends into the interior of the material removal element 16 a specific, predetermined distance which limits the radial expansion of the braided wires 102 by a corresponding distance. In other words, the proximal end 118 of the distal annulus 106 of the construction 116 can travel a maximum distance smaller than the distance traveled by the proximal end 118 of the distal annulus 106 of the embodiments of FIGS. 1, 4, and 5 upon maximum proximal movement of the bead 120 and the guidewire 42. Contact between the proximal end 118 of the distal annulus 106 and the distal end 98 of the inner coil 94 positively limits axial compression and radial expansion of the material removal element 16. Once the proximal end 118 engages the distal end 98, the removal element 16 cannot be further axially compressed because the guidewire 42 and the bead 120 cannot be moved further proximally. Thus, the material removal element 16 of the construction 116 can radially expand a predetermined maximum distance smaller than the maximum distance of radial expansion of the material removal element 16 of the embodiments of FIGS. 1, 4 and 5.

Another construction 126 of the distal portion of the vascular occlusion material removal device 10 is shown in FIG. 7. This construction 126 utilizes material removal element radial expansion limiting means in the form of elongated windings 128 on a portion of the inner coil 94 that extends into the interior of the material removal element 16 in much the same manner as discussed hereinabove with respect to the construction 116. However, in this construction 126, the distal end 98 of the of the inner coil 94 is fixedly attached to the distal annulus 106 by solder, weld, braze or similar means. Thus, when the guidewire 42 is moved proximally and the fillet 122 engages the distal annulus 106, the expanded windings 128 within the hollow interior of the material removal element 16 are compressed until adjacent windings 130A and 130B on opposite sides of each of the expanded windings 128 contact each other. In this manner, the axial compression and the radial expansion of the braided material removal element 16 are positively limited by the sum of the distances between the adjacent windings 130A and 130B within the interior of the material removal element 16 when the material removal element 16 is in the relaxed, contracted position as shown.

Yet another embodiment of the material removal element radial expansion limiting means is shown in FIG. 8. Here, the means takes the form of two tubes 132 and 134, such as hypotubes and the like. The tube 132 is fixedly attached to an inner surface of the distal-most windings of the inner coil 94 by suitable means, such as adhesive, solder, braze or weld, and is also attached by similar means to the proximal annulus 104. This insures proper torque transfer from the drive shaft 92 to the material removal element 16. The tube 132 extends into the hollow interior of the material removal element 16 a certain, predetermined distance to locate a distal end 136 of the tube 132 within the hollow interior.

The tube 134 is fixedly attached to the distal annulus 106 by similar means, and extends proximally into the hollow interior of the material removal element 16 to locate a proximal end 138 of the tube 134 within the hollow interior. Thus, the distal end 136 of the tube 132 is offset from the proximal end 138 of the tube 134 by a predetermined distance which limits axial compression of the radially expandable material removal element 16. The tubes 132 and 134 both have inner diameters sufficient for accepting the guidewire 42 therethrough so that the material removal element 16 of this embodiment radially expands in the same manner as the other embodiments. As the guidewire 42 and the bump 124 move proximally, the bump 124 engages the distal annulus 106 and forces the distal annulus 106 and the tube 134 proximally. The braided wires 102 expand radially until the distal end 136 of the tube 132 contacts the proximal end 138 of the tube 134. This contact positively limits radial expansion of the material removal element 16. Thus, the lengths of both tubes 132 and 134 and the distance between the distal end 136 and the proximal end 138 determine the maximum radial expansion of the material removal element 16.

An additional embodiment of the material removal element radial expansion limiting means is contained in the construction 140 of FIG. 9. Here, the tube 134 is eliminated and the tube 132 is elongated with respect to the embodiment of FIG. 8. When the material removal element 16 is expanded fully, the proximal end 118 of the distal annulus 106 engages the distal end 136 of the tube 132. Thus, the length of the tube 132 and the distance between the distal end 136 of the tube 132 and the proximal end 118 of the distal annulus 106 within the hollow interior of the material removal element 16 determine and positively limit the maximum radial expansion of the material removal element 16.

In some cases, it may be desirable to perform balloon angioplasty in conjunction with vascular occlusion material removal. Because of this desire, another embodiment of the invention, an expandable intravascular occlusion removal device 142, is provided and is shown in FIG. 10. The removal device 142 is substantially similar to the removal device 10, except for the differences noted in the following paragraphs, hence the like reference numerals for similar structures. While the removal device 142 is illustrated as having the lock knob 54 and the thumb pad 66, it is to be remembered that the elements of the various embodiments of the invention can be combined in any desired fashion.

The removal device 142 includes a novel manifold assembly 144 and a novel catheter assembly 146 which differ from the catheter assembly 14 and the manifold assembly 22. Specifically, the manifold assembly 144 includes a third port 148 located distally of the port 82. The port 148 is connectable with a suitable source of fluid, not shown, but known in the art, for supplying the catheter assembly 146 with fluid to dilate a dilating member 158 for performing balloon angioplasty. The port 148 is located distally of a proximal end 150 of the catheter assembly 146.

The catheter assembly 146 includes a catheter sheath 152 having at least two lumens: a drive shaft lumen 154 and a fluid inflation lumen 156. The drive shaft 92 extends through the drive shaft lumen 154 from the distal end 34 of the drive shaft 26 to the proximal annulus 104, and the drive shaft lumen 154 can be utilized for infusion and aspiration in much the same manner as the catheter sheath 90 can. The drive shaft lumen 154 extends substantially the entire length from the manifold assembly 144 to the proximal annulus 104.

A dilating member 158, constructed substantially similarly to an angioplasty balloon, is located on the catheter assembly 146 offset proximally of a distal end 160 of the catheter assembly 146 and the distal end of the drive shaft lumen 154. The inflation lumen 156 extends from the port 148 to a proximal end 162 of the dilating member 158 and conveys fluid from the fluid source, conventionally referred to as an inflation device, to and from the dilating member 158, thereby causing the dilating member 158 to inflate and deflate. To facilitate intravascular location of the dilating member 158, a radiopaque marker band 164 is provided on the outer surface of the drive shaft lumen 154, thereby rendering the intravascular portion of the dilating member 158 radioscopically visible to a treating physician. Intravascular inflation of the dilating member 158 provides added stability to the distal portion of the removal device 142 during operation thereof, while also allowing the treating physician to occlude blood flow through the vascular lumen being treated and further allowing the physician to perform balloon angioplasty if desired. With the removal device 142 it is possible for a treating physician to cut, remove, and/or angioplastically displace vascular occlusion material while only using a single piece of equipment.

The various embodiments of the present invention also provide a number of novel methods for performing intravascular treatments, such as removing or displacing vascular occlusion material. These methods comprise a plurality of steps, some of which have been discussed in detail already, so the following discussion of the novel methods will simply refer back to those detailed discussions, instead of restating them, where appropriate.

The expandable intravascular occlusion material removal device 10 or 142 is inserted into the patient's vascular system through a suitable puncture or other access site, such as via the femoral artery, in well known fashion. At this point, the expandable material removal element 16 is in the radially contracted position shown in FIG. 4. Because the removal device 10 or 142 has a low profile when the material removal element 16 is in the contracted position, the intravascular portion of the removal device 10 or 142 can be inserted through a conventional 7 French guide catheter, well known to those having ordinary skill in the relevant art. The removal device 10 or 142 is moved over the medical guidewire 42, which has been previously positioned in proximity to the intravascular treatment site, until the distal end of the annulus 106 is adjacent the proximal end of the bearing surface 112, as discussed hereinabove. Now, the expandable material removal element 16, currently in the contracted position, is located in close proximity to the vascular occlusion material to be removed thereby.

At any time, a fluid, such as saline, a drug therapy, and the like, can be applied to the port 80 on the manifold assembly 22 or 144 from a suitable fluid source. The fluid flows through the port 80 and into the portion of the main lumen 78 located between the fluid seal 84 and 86, and from there, through the aperture 88 into the hollow interior of the drive shaft 92. The fluid flows along the axial length of the drive shaft 92 and passes into the hollow interior defined by the braided wires 102 of the expandable material removal element 16. The fluid can flow through spaces between adjacent portions of the braided wires 102 to infuse the intravascular treatment site with fluid. This may provide for maintenance of fluid within a vascular lumen if aspiration is used.

At any time, another fluid to be infused into the patient, or a negative pressure to aspirate the intravascular treatment site may be applied to the port 82 from a suitable source. The fluid or the negative pressure is applied through the port 82 to the hollow interior of the catheter sheath 90 or 152, and from there to the vascular lumen adjacent the distal end 18 or 160 of the catheter assembly 14 or 146, respectively. Because of the relative locations of the distal ends of the drive shaft 92 and the catheter sheath 90 or 152, as discussed earlier, effective aspiration of the treatment site may be provided. This is important because some vascular occlusion material, such as certain types of thrombus, can be removed from a vascular surface or another occlusion simply by aspiration.

With the expandable material removal element 16 being properly positioned with respect to the vascular occlusion material to be removed, the treating physician can expand the material removal element 16 to the desired degree by implementing the methods discussed earlier with respect to the guidewire lock mechanism 50 and the material removal element expansion control mechanism 52. The material removal element 16 can be moved into a plurality of positions by variably expanding and/or contracting the material removal element 16. Thus, multiple material removal element 16 sizes, shapes, profiles and characteristics may be achieved with the use of a single occlusion material removal device 10 or 142. The controlled, incremental expansion and contraction of the expandable material removal element 16 can provide a treating physician with greater flexibility in performing intravascular treatments, as well as possibly reducing the costs of such treatments because multiple pieces of equipment need not be used. This is a significant improvement over some of the intravascular treatment devices of the prior art. In addition, the various constructions of the material removal element radial expansion limiting means can insure that the material removal element 16 is not over-expanded, thereby possibly reducing the chances of injury to a patient.

With the removal device 142, either before of after expansion of the expandable material removal element 16, the dilating member 158 can be inflated to a suitable pressure by application of a pressurized fluid to the port 148, as discussed above. The pressurized fluid flows through the port 148 and the lumen 156, and into the interior of the dilating member 158. The dilating member 158 expands sufficiently so that an outer surface thereof engages the interior surface of the vascular lumen. The dilating member 158 can be inflated to pressures on the order of 4 to 8 atmospheres and can center and stabilize distally-located portions of the removal device 142 during operation thereof. Inflation of the dilating member 158 can also be used to occlude blood flow through the vasculature being treated.

The removal device 10 or 142 is now ready to remove vascular occlusion material from a vascular surface or from a vascular occlusion by expansion and/or rotation of the expandable material removal element 16. It is to be noted that, because the expandable material removal element 16 is comprised of braided wires 102 which define spaces between adjacent wires 102, expansion of the material removal element 16 may not occlude fluid flow through the vascular lumen. Fluids infused into the vasculature by the device 142 at a location distally of the dilating member 158 can flow around and through the spaces between the braided wires 102 and continue through the patient's vasculature distally of the material removal element 16.

If the occlusion material were located radially above the material removal element 16, then appropriate expansion of the wires 102 can allow the abrasive 105 or other cutting surface on the wires 102 to bite into a portion of the occlusion material. This radial cutting of the wires 102 into the vascular occlusion material can cause a portion of the material to pass through spaces between adjacent wires 102 and be captured in the hollow interior of the material removal element 16 defined by the wires 102. The expansion of the braided wires 102 defines a radially directed cutting vector for severing occlusion material. The effectiveness of this radial cutting may depend upon the composition or hardness of the vascular occlusion material. If desired, the expandable material removal element 16 can be moved into the contracted position, thereby trapping occlusion material within the hollow interior defined by the braided wires 102. The material removal element 16 can be removed from the patient's vasculature if desired and the occlusion material will be retained within the hollow interior of the material removal element 16 because of the spring-like forces inherent in the wires 102. The captured material can be later retrieved for performing a biopsy or other procedure on the material.

Some occlusion material may not be susceptible to removal in this fashion. For instance, some occlusion material may be relatively hard or calcified, thereby making it rather difficult for the wires 102 to bite into the material upon expansion of the material removal element 16. If this is the case, then the material removal element 16 can be expanded such that the outer surfaces of the braided wires 102 contact the interior surface defined by the occlusion. In other words, the material removal element 16 is expanded to define a cutting diameter slightly larger than a non-occluded diameter of a particular portion of the vasculature. By expanding the diameter of the removal element 16 to a size slightly larger than the non-occluded diameter of the vascular lumen, more effective and more efficient removal of occlusive material is provided as compared to some prior art methods whereacutting element is expanded to define a diameter equal to that of the vascular lumen. The material removal element 16 is expanded and is locked in this expanded position according to the method described earlier with respect to the guidewire lock mechanism 50 and the material removal element expansion control mechanism 52. The maximum radial expansion of the material removal element 16 is limited by the radial expansion limiting means discussed hereinabove.

Once properly locked in the expanded position, the treating physician actuates the control switch 30, thereby energizing the motor 24. The motor 24 induces rotation of the drive shaft 26, which, in turn, causes the drive shaft 92 to rotate within the catheter sheath 90 or 152. The material removal element 16 is also rotated conjointly with the drive shafts 26 and 92. The rotation of the material removal element 16 enables the sharp edges or abrasive 105 particles on the surfaces of the braided wires 102 to cut, abrade, ablate, or otherwise remove vascular occlusion material from a vascular lumen surface or a vascular occlusion.

Rotation of the braided wires 102 defines a cutting vector directed tangentially to the surface interface between a given wire 102 and the occlusion material. The removed occlusion material can pass through the spaces between adjacent wires 102 and be caught in the hollow interior defined by the braided wires 102 comprising the material removal element 16. This removed material can be trapped within the material removal element 16 upon contraction thereof, as described earlier, and subsequently removed from the patient's vasculature along with the material removal element 16. Alternatively, the removed vascular occlusion material can be drawn into the interior of the catheter sheath 90 or 152 by means of negative pressure applied to the port 148. Thus, there are at least two ways by which removed vascular occlusion material can be carried away from the patient's vasculature.

After a sufficient amount of vascular occlusion material has been removed by rotation of the material removal element 16, the non-occluded diameter of the vascular lumen is enlarged, but further occlusive material may remain within the vascular lumen. It may be desirable to remove more occlusion material, thereby further enlarging the non-occluded diameter of the vascular lumen. To do this, the expandable material removal element 16 is further radially expanded, according to the steps of the method discussed earlier, to define a cutting diameter slightly larger than this second, non-occluded diameter of the vascular lumen. This process of expanding the cutting diameter of the material removal element 16 progressively—starting small and finishing large—can be repeated as often as necessary until a non-occluded diameter of the desired length is formed in the vascular lumen. This progressive cutting process allows for more efficient removal of the occluding material by always using a cutting diameter just slightly larger than the non-occluded diameter. The expandable nature of the material removal element 16 allows this process to be executed while utilizing only one intravascular device 10 or 142.

It is possible that a particular vascular lumen might have more than one occlusion which may be located distally of a first occlusion. If this is the case after sufficient material of the first occlusion is removed to revascularize that portion of the lumen, then the material removal element 16 can be repositioned intravascularly adjacent a second occlusion for removing its occluding material. To reposition the material removal element 16, the dilating member 158, if inflated, should be deflated. The material removal element 16 should also be moved into the contracted position. The material removal element 16, the dilating member 158 and the distal portion of the catheter assembly 14 and 146 assume a low profile for facilitating intravascular movement of the removal device 10 or 142. The entire removal device 10 or 142 can now be freely repositioned for removing material from the second occlusion. It is envisioned that, in some embodiments of the invention, the drive shaft 92 and the cutting element 16 may be axially shiftable with respect to the catheter sheath 90, thereby facilitating intravascular repositioning of the removal element 16.

Once properly positioned adjacent the second occlusion, the material removal element 16 can be expanded as before and the same process of occlusion material removal can be performed. There may be some occlusions, however, which define a non-occluded diameter smaller than the outer diameter defined by the braided wires 102 in the contracted position. This can prevent effective cutting contact between the wires 102 and the occlusion material. However, if the non-occluded diameter were large enough to accept the coil 114 of the guidewire 42 and the bearing surface 112, then the occlusion material can still be removed by the material removal element 16.

In this case, the coil 114 of the guidewire 42 and the bearing surface 112 are passed through the non-occluded diameter sufficiently to bring the cutting surface 108 on the distal annulus 106 into contact with a proximal end of the occlusion. The cutting surface 108 has a configuration or an abrasive 105 coating which facilitates removal of vascular occlusion material upon rotation of the distal annulus 106. In addition, as the figures show, the cutting surface 108 is tapered so that a relatively smaller cutting diameter encounters the occlusion material initially.

The motor 24 is energized, thereby rotating the material removal element 16 and the distal annulus 106, and the cutting surface 108 begins to bore through the occlusion material. The cutting action of the cutting surface 108 is directed substantially longitudinally or axially within the vascular lumen, and the cutting surface 108 can grind away occlusion material from the occlusion or the vascular surface, thereby increasing the size of the non-occluded diameter in the vascular lumen. Of course, aspiration can be used to carry the removed material away from the patient. The treating physician can apply an axially directed force to the removal device 10 or 142 as the cutting surface 108 rotates to move the cutting surface 108 distally through the occlusion. Since the cutting surface 108 is tapered, a progressively larger cutting diameter is engaged against the vascular occlusion as the cutting surface 108 and the associated removal device 10 or 142 are moved distally within the vascular lumen. Thus, the cutting surface 108 also executes substantially the same occlusion material removal process described above by starting with a small cutting diameter and gradually increasing that diameter as progressively more occluding material is removed.

The cutting surface 108 is rotated against the occlusion and simultaneously advanced distally with respect to the occlusion to form an enlarged diameter pilot hole longitudinally through the occlusion. As more proximal portions of the cutting surface 108 encounter the occlusion material, the cutting surface 108 may cut occlusion material along vectors directed tangentially to the interface of the cutting surface 108 and the occlusion. It is to be noted that a proximal-most portion of the cutting surface 108 defines an outer diameter substantially equal to the outer diameter defined by the braided wires 102 when in the contracted position of FIG. 4. Thus, the pilot hole formed by the cutting surface 108 has dimensions sufficient for accepting the material removal element 16 in the contracted position. Therefore, once this pilot hole has been formed, the motor 24 can be stopped, which ceases rotation of the material removal element 16 and the cutting surface 108. The expandable material removal element 16 can be positioned within the pilot hole and the dilating member 158, if provided, can be expanded to provide added stability to the distally-located portions of the device 142 or to occlude blood flow through the vascular lumen. At this point, the expandable material removal element 16 can be expanded, according to the above-discussed process, within the pilot hole so that the braided wires 102 engage the occlusion material. The motor 24 can again be energized, and the rotating material removal element 16 can remove additional occluding material. Of course, because the guidewire 42 moves independently of the drive shafts 26 and 92, the removal element 16 can also be expanded while the motor 24 is running.

In any case, once sufficient occlusion material has been removed, it may be desirable to perform balloon angioplasty within the vascular lumen in order to displace any remnants of the occlusion. To perform both occlusion material removal and angioplastic displacement of an occlusion remnant, the removal device 142 is used. After the motor 24 and the rotation of the expandable material removal element 16 has been stopped, the material removal element 16 is moved into the contracted position so that the braided wires 102 of the removal device 142 define a low profile. If the dilating member 158 was expanded during operation of the material removal element 16, then it too should be deflated, by reversing the above-discussed pressure flow, so that the entire distal portion of the removal device 142 defines a low profile for facilitating intravascular movement of the removal device 142.

The catheter assembly 146 of the removal device 142 is shifted distally within the vascular lumen to locate the contracted dilating member 158 adjacent the remnants of the occlusion. The treating physician may have an easier time of properly positioning the dilating member 158 with respect to the occlusion remnants because the marker band 164 renders the position of the dilating member 158 radioscopically visible. Once proper position has been attained, the dilating member 158 can be inflated, as discussed above, to a sufficient pressure, typically on the order of 4 to 8 atmospheres, to displace the remnants and further revascularize the vascular lumen.

A further novel method of removing occlusion material begins with locating the removal element 16, in the contracted position, distally of the occlusion material. The removal element 16 is expanded, as described above, and is then shifted proximally in the lumen towards the occlusion. The removal element 16 may be energized such that the rotating removal element 16 removes occlusion material from a distal end thereof upon contact with the occlusion. The removal element 16 can be moved proximally progressively until sufficient occlusion material has been removed to revascularize the lumen.

According to another novel method for removing vascular occlusion material, the removal element 16 can be inserted into a vascular lumen and positioned proximally of an vascular occlusion. The removal element 16 can then be expanded, by use of the above-discussed methods, to a certain diameter, such as the diameter of a non-occluded portion of the lumen, and advanced within the lumen towards the occlusion. The removal element 16 is forced into contact with the occlusion, and the wires 102 forming the expanded braid 96 bite into the occlusion material. The removal element 16 is then retracted from the occlusion and readied for another advance towards the occlusion. At any point, the removal element 16 can be collapsed and retracted, as may be desirable to determine the composition of the occlusion material, or may be contracted or further expanded, such as discussed above, to define different cutting diameters. The steps of this method can be repeated as often as desired.

Still a further method according to the teachings of the present invention takes advantage of a novel property provided by the removal element 16, viz. the removal element 16 can absorb forces applied to it and correspondingly deform or deflect. This novel property may be more readily understood with reference to FIG. 11. FIG. 11 illustrates a cross section of a vascular lumen 166 occluded by occluding material 168. The occluding material 168 defines an eccentric surface 170 offset from the vascular lumen 166 by a distance which defines a non-occluded diameter in the vascular lumen 166. The removal element 16 is inserted into the non-occluded diameter and expanded, as discussed above, until an outer surface of the removal element 16 contacts the eccentric surface 170. Because the removal element 16 can absorb forces applied to it, such as those attendant with expansion or rotation of the removal element 16, the removal element 16 deflects or deforms such that the removal element 16 defines a configuration which complements the corresponding configuration of the eccentric surface 170. Thus, the removal element 16 can take into account varying occlusion morphology.

Once the removal element 16 has assumed the complementing configuration, the motor 24 is activated and the removal element 16 begins to rotate within the non-occluded diameter. Deflection of the braid 96 formed by the wires 102 causes longitudinal or axial and radial cutting actions or vectors to be reduced correspondingly. This may reduce the probability that healthy tissues might be removed because a cushioned, softer engagement may be formed between the healthy tissues and the removal element 16 due to the spring-like nature of the removal element 16. In addition, because the configuration of the removal element 16 conforms to the configuration of the occlusion material 168, upon rotation of the element 16, a greater concentration of removing forces can be generated at an area, indicated generally by reference numeral 172, on the occlusion material 168 than the force concentration present at an area 174 on the vascular lumen 166. Specifically, cutting forces may be evenly distributed over the area 174. This can lead to more efficient removal of vascular occlusion material 168.

Furthermore, it is to be noted that the spring-like nature of the removal element 16 provides for another novel method for removing vascular occlusion material. Specifically, according to this method, the removal element 16 may be placed within a lumen constricted or reduced by an occlusion such that the braid 96 is in proper position with respect to the occlusion for removal of occlusion material 168. At this point, the wire lock mechanism 50 and the removal element expansion control mechanism 52 can be actuated, as described hereinabove, in order to expand the removal element 16 to define a diameter equal to a non-occluded diameter of the same vascular lumen, i.e. the diameter of the vascular lumen with the occlusion material removed.

The removal element 16 expands to define a configuration which corresponds to the configuration of the eccentric surface 170, as shown in FIG. 11. However, because the occlusion material 168 prevents the removal element 16 from immediately expanding to define the non-occluded diameter, the braid 96 absorbs and stores expanding forces in the form of spring energy. This stored spring energy allows the removal element 16 to be essentially self-expanding during operation of the removal device 10 or 142.

Specifically, the motor 24 is energized and the removal element 16 begins to rotate within the lumen 166, thereby removing vascular occlusion material 168 from the occlusion. As progressively more and more occlusion material 168 is removed from the occlusion, the spring energy stored within the braid 96 is released, and causes the removal element 16 to expand further responsive to the amount of occlusion material 168 removed. The stored spring energy is progressively released as greater amounts of occlusion material 168 are removed until the braid 96 is expanded to the degree indicated by the removal element expansion control mechanism 52. The removal element expansion limiting means also insures that the removal element 16 is not overexpanded. The removal element 16 ceases to expand once sufficient occlusion material 168 has been removed and once sufficient stored spring energy has been released. At this point, the diameter defined by the expanded braid 96 should be approximately equal to the original, non-occluded diameter of the vascular lumen 166.

The self-expanding nature of the removal element 16 provides another novel method of removing vascular occlusion material from a vascular lumen. According to this method, the removal element 16 is pre-formed or expanded such that the element 16 defines a certain, pre-determined configuration. By placing the removal element 16 in this configuration, the element 16 is provided with a memory of this shape. Forming the element 16 with shape memory alloys, such as nitinol and the like, also insures effective shape or configuration memory. The pre-formed configuration preferably has dimensions suitable for intravascular insertion and navigation. The pre-formed removal element 16 is positioned adjacent the occlusion material, which defines a non-occluded diameter within the vascular lumen. The removal element 16 is then inserted into the non-occluded lumen.

Contact of the removal element 16 with the occlusion material imparts forces to the braided wires 102 which deform the configuration of the removal element 16. The spring-like nature of the braided wires 102 comprising the removal element 16 allows the element 16 to deform or otherwise comply to a configuration defined by the occlusion material, as illustrated in FIG. 11. The element 16 can now be energized so that occlusion material can be removed. As progressively more occlusion material is removed, the shape memory of the wires 102 allows the element 16 to move towards the initial, pre-determined configuration. Once sufficient occlusion material has been removed, the memory aspects of the removal element 16 allow it to recover from its deformed state to its original configuration.

As is evident from the foregoing discussion, the embodiments of the present invention provide treating physicians with a number of novel methods for performing intravascular treatments. The individual steps comprising these methods can be performed in any order, and the steps of one method can be interspersed with steps of other methods to achieve desired results. By providing an expandable material removal element 16, the embodiments of the invention provide a plurality of material removal element 16 sizes, shapes and cutting profiles or characteristics combined in a single intravascular occlusion material removal device 10 or 142. These shapes, sizes and characteristics are positively variable by the controlled incremental expansion of the material removal element 16 offered by the guidewire lock mechanism 50 and the material removal element expansion control mechanism 52. Also, the various constructions of the material removal element radial expansion limiting means prevents over-expansion of the material removal element 16.

By combining the material removal element 16 with the cutting surface 108, a plurality of differently directed cutting actions can be performed by the removal devices 10 and 142. Specifically, the material removal element 16 is capable of producing cutting actions directed radially and tangentially with respect to the vascular lumen or occlusion. In addition, the cutting surface 108 can produce cutting actions directed tangentially and longitudinally with respect to the vascular lumen or occlusion. Thus, at least three differently directed cutting actions can be produced by the removal device 10 or 142. In addition, the occlusion material can be cut, ground, displaced, captured or aspirated. Specifically, relatively soft occlusion material can be sliced or cut by the wires 102 and fall into the hollow interior of the removal element 16, while relatively hard occlusion material can be ground by the abrasive 105 on the wires 102. Thus, a treating physician can have greater flexibility in performing intravascular treatments while using only one device 10 or 142.

While preferred embodiments of the present invention are shown and described, it is envisioned that those skilled in the art may devise various modifications of the present invention without departing from the spirit and scope of the appended claims.

We claim:

1. A method for removing vascular occlusion material from a vascular lumen comprising the steps of:

providing a vascular occlusion material removal device having an expandable occlusion material removal element, the material removal element comprising a braid having a hollow interior;

providing a guide wire with a bearing surface located distally thereon which operatively engages an end of the material removal element to cause longitudinal contraction thereof when the guide wire is longitudinally shifted with respect to the material removal element;

intravascularly navigating the guide wire to the occlusion material;

intravascularly navigating the braid to the occlusion material over the guide wire;

shifting the guide wire with respect to the braid to expand the braid;

expanding the braid such that the braid bites into occlusion material, thereby allowing occlusion material to pass into the hollow interior; and shifting the guide wire with respect to the braid to contract the braid and to capture occlusion material within the hollow interior.

2. A method for removing vascular occlusion material as defined in claim 1, further comprising the step of:

withdrawing the braid from the patient to remove occlusion material captured in the hollow interior from the patient.

3. A method for removing vascular occlusion material as defined in claim 1, further comprising the step of:

rotating the braid intravascularly to remove vascular occlusion material.

4. A method for removing vascular occlusion material as defined in claim 1, further comprising the steps of:

providing a means on the removal device for positively limiting expansion of the braid; and positively limiting expansion of the braid intravascularly by use of the means.

5. A method for removing vascular occlusion material as defined in claim 1, further comprising the steps of:

providing a catheter sheath having a distal end on the removal device insertable intravascularly into the patient, such that the distal end of the catheter sheath is located proximally of the braid;

applying a negative pressure to the catheter sheath; and aspirating removed vascular occlusion material through the catheter sheath by means of the negative pressure.

6. A method for removing vascular occlusion material as defined in claim 5, further comprising the steps of:

applying a fluid to the catheter sheath; and infusing the fluid into the patient through the catheter sheath.

7. A method for removing vascular occlusion material from a vascular lumen comprising the steps of:

providing a vascular occlusion material removal device having an expandable and flexible occlusion material removal element;

providing a guide wire with a bearing surface located distally thereon which operatively engages an end of the material removal element to cause longitudinal contraction thereof when the guide wire is longitudinally shifted with respect to the material removal element;

intravascularly navigating the guide wire to the occlusion material;

inserting the guide wire into the removal element;

intravascularly navigating the removal element to the occlusion material over the guide wire;

shifting the guide wire with respect to the removal element to expand the removal element intravascularly;

energizing the removal element intravascularly to remove vascular occlusion material;

applying a fluid to the removal device; and irrigating the vascular lumen with the fluid.

8. A method according to claim 7, wherein the material removal device includes a hollow drive shaft insertable intravascularly and operatively connected to the removal element for energizing the removal element, and further comprising the steps of:

applying a fluid to the hollow drive shaft; and irrigating the vascular lumen with the fluid.

9. A vascular occlusion material removal device for removing vascular occlusion material in a vascular lumen, the removal device comprising:

a prime mover;

an expandable material removal element insertable intravascularly into the vascular lumen, the expandable material removal element comprising a plurality of braided wires;

a hollow drive shaft operatively connecting the prime mover to the expandable material element for rotating the expandable material removal element intravascularly;

a guide wire insertable through the expandable material removal element and the hollow drive shaft;

the guide wire having a bearing surface located distally thereon which operatively engages an end of the material removal element to cause longitudinal contraction thereof when the guide wire is longitudinally shifted with respect to the material removal element;

the guide wire being shiftable within the drive shaft and the expandable material removal element;

the expandable material removal element being expandable responsive to shifting of the guide wire;

a material removal element movement control mechanism operatively connected to the guide wire for positively shifting the guide wire; and a guide wire lock mechanism operatively connected between the guide wire and the material removal element movement control mechanism for fixing the guide wire with respect to the material removal element movement control mechanism.

10. A vascular occlusion material removal device as defined in claim 9, further comprising at least one of 8 and 16 braided wires.

11. A vascular occlusion material removal device as defined in claim 9, wherein the wires are made of a superelastic alloy.

12. A vascular occlusion material removal device as defined in claim 9, further comprising an abrasive disposed on the wires.

13. A vascular occlusion material removal device as defined in claim 12, wherein the abrasive comprises a diamond grit electroplated onto the wires.

14. A vascular occlusion material removal device for removing vascular occlusion material in a vascular lumen, the removal device comprising:

a prime mover;

an expandable material removal element insertable intravascularly into the vascular lumen;

a hollow drive shaft operatively connecting the prime mover to the expandable material removal element for rotating the expandable material removal element intravascularly, the drive shaft comprising a cylindrical portion having a hollow interior and a coiled portion;

an aperture in the cylindrical portion for allowing fluid to flow into the hollow interior of the cylindrical portion;

a guide wire insertable through the expandable material removal element in the hollow drive shaft;

the guide wire having a bearing surface located distally thereon which operatively engages an end of the material removal element to cause longitudinal contraction thereof when the guide wire is longitudinally shifted with respect to the material removal element;

the guide wire being shiftable within the drive shaft and the expandable material removal element;

the expandable material removal element being expandable responsive to shifting of the guide wire;

a material removal element movement control mechanism operatively connected to the guide wire for positively shifting the guide wire; and a guide wire lock mechanism operatively connected between the guide wire and the material removal element movement control mechanism for fixing the guide wire with respect to the material removal element movement control mechanism.

15. A vascular occlusion material removal device as defined in claim 14, wherein the cylindrical portion has a proximal end; further comprising a fluid seal located at the proximal end of the cylindrical portion for limiting fluid flow proximally of the proximal end of the cylindrical portion.

16. A vascular occlusion material removal device for removing vascular occlusion material in a vascular lumen, the removal device comprising:

a prime mover;

an expandable material removal element insertable intravascularly into the vascular lumen;

a hollow drive shaft operatively connecting the prime mover to the expandable material removal element for rotating the expandable material removal element intravascularly, the hollow drive shaft comprising a coil;

a guide wire insertable through the expandable material removal element and the hollow drive shaft;

the guide wire having a bearing surface located distally thereon which operatively engages an end of the material removal element to cause longitudinal contraction thereof when the guide wire is longitudinally shifted with respect to the material removal element;

the guide wire being shiftable within the drive shaft and the expandable material removal element;

the expandable material removal element being expandable responsive to shifting of the guide wire;

a material removal element movement control mechanism operatively connected to the guide wire for positively shifting the guide wire; and a guide wire lock mechanism operatively connected between the guide wire and the material removal element movement control mechanism for fixing the guide wire with respect to the material removal element movement control mechanism.

17. A vascular occlusion material removal device as defined in claim 16, wherein the drive shaft further comprises a lubricous sheath overlying the coil.

18. A vascular occlusion material removal device for removing vascular occlusion material in a vascular lumen, the removal device comprising:

a prime mover;

an expandable material removal element insertable intravascularly into the vascular lumen;

a hollow drive shaft operatively connecting the prime mover to the expandable material removal element for rotating the expandable material removal element intravascularly;

a guide wire insertable through the expandable material removal element in the hollow drive shaft;

the guide wire having a bearing surface located distally thereon which operatively engages an end of the material removal element to cause longitudinal contraction thereof when the guide wire is longitudinally shifted with respect to the material removal element;

the guide wire being shiftable within the drive shaft and the expandable material removal element;

the expandable material removal element being expandable responsive to shifting of the guide wire;

a material removal element movement control mechanism operatively connected to the guide wire for positively shifting the guide wire;

a guide wire lock mechanism operatively connected between the guide wire and the material removal element movement control mechanism for fixing the guide wire with respect to the material removal element movement control mechanism; and a dilating member on the device for performing at least one of centering the device intravascularly, stabilizing the device intravascularly, occluding flow through a vascular lumen, and angioplastically displacing occlusion material.

19. A vascular occlusion material removal device for removing vascular occlusion material in a vascular lumen, the removal device comprising:

an expandable material removal element insertable intravascularly into a patient;

a guide wire insertable through the expandable material removal element;

the guide wire having a bearing surface located distally thereon which operatively engages an end of the material removal element to cause longitudinal contraction thereof when the guide wire is longitudinally shifted with respect to the material removal element;

the guide wire being shiftable within the material removal element;

the material removal element being expandable responsive to shifting of the guide wire;

the removal element comprising a plurality of braided wires; and an abrasive disposed on the wires for removing vascular occlusion material.

20. A vascular occlusion material removal device for removing vascular occlusion material in a vascular lumen, the removal device comprising:

an expandable material removal element insertable intravascularly into a patient;

a guide wire insertable through the expandable material removal element;

the guide wire having a bearing surface located distally thereon which operatively engages an end of the material removal element to cause longitudinal contraction thereof when the guide wire is longitudinally shifted with respect to the material removal element;

the guide wire being shiftable within the material removal element;

the material removal element being expandable responsive to shifting of the guide wire;

the removal element comprising a plurality of braided wires; and the wires being made from a super-elastic alloy.

21. A vascular occlusion material removal device as defined in claim 20, wherein the super-elastic alloy is nitinol.

22. A method for removing vascular occlusion material from a vascular lumen comprising the steps of:

providing a vascular occlusion material removal device having an expandable occlusion material removal element, wherein the removal element comprises a plurality of braided wires, further comprising an abrasive disposed on the wires;

providing a guide wire having a bearing surface located distally thereon which operatively engages an end of the material removal element to cause longitudinal contraction thereof when the guide wire is longitudinally shifted with respect to the material removal element;

intravascularly positioning the guide wire distally of the occlusion material;

inserting the guide wire into the removal element;

intravascularly positioning the removal element over the guide wire distally of the occlusion material;

shifting the guide wire with respect to the removal element to expand the element intravascularly; and moving the removal element proximally within the vascular lumen to remove occlusion material.

23. A method according to claim 22, further comprising the step of: rotating the removal element intravascularly.

24. An over-the-wire vascular occlusion material removal device for removing vascular occlusion material from a vascular lumen, the removal device comprising:

a flexible vascular occlusion material removal element insertable intravascularly into the vascular lumen for removing vascular occlusion material, the removal element comprising a plurality of shape memory alloy braided wires;

a configuration defined by the removal element;

the removal element having a memory of the configuration;

the removal element being deformable; and wherein the memory is sufficient to allow the removal element to return towards the configuration.

25. A vascular occlusion material removal device as defined in claim 24, wherein the shape memory alloy is nitinol.

* * * * *